United States Patent
Rehman et al.

(10) Patent No.: US 11,577,037 B2
(45) Date of Patent: Feb. 14, 2023

(54) AUTOMATIC DETECTION OF AIRWAY DEVICE, ENDOTRACHEAL INTUBATION, AND TUBE MISPLACEMENT IN CHILDREN DURING THE ANESTHESIA PROCEDURE

(71) Applicant: The Children's Hospital of Philadelphia, Philadelphia, PA (US)

(72) Inventors: Mohamed Rehman, Philadelphia, PA (US); Ali Jalali, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 965 days.

(21) Appl. No.: 16/344,447

(22) PCT Filed: Oct. 25, 2017

(86) PCT No.: PCT/US2017/058252
§ 371 (c)(1),
(2) Date: Apr. 24, 2019

(87) PCT Pub. No.: WO2018/081245
PCT Pub. Date: May 3, 2018

(65) Prior Publication Data
US 2020/0261675 A1 Aug. 20, 2020

Related U.S. Application Data

(60) Provisional application No. 62/412,508, filed on Oct. 25, 2016.

(51) Int. Cl.
*A61M 16/00* (2006.01)
*A61M 16/04* (2006.01)
(Continued)

(52) U.S. Cl.
CPC ...... *A61M 16/026* (2017.08); *A61M 16/0051* (2013.01); *A61M 16/01* (2013.01);
(Continued)

(58) Field of Classification Search
CPC ............ A61M 16/026; A61M 16/0411; A61M 16/085; A61M 16/0051; A61M 16/01;
(Continued)

(56) References Cited

U.S. PATENT DOCUMENTS 6,839,753 B2 1/2005 Biondi et al.
2006/0278221 A1 12/2006 Schermeier et al.
(Continued)

FOREIGN PATENT DOCUMENTS

WO 2011041838 A1 4/2011

OTHER PUBLICATIONS

International Preliminary Report on Patentability for International Application No. PCT/US2017/058252, dated Apr. 30, 2019—6 pages.
(Continued)

*Primary Examiner* — Steven O Douglas
(74) *Attorney, Agent, or Firm* — RatnerPrestia

(57) ABSTRACT

Algorithms for detecting endotracheal intubation and/or misplacement of endotracheal tubes in child patients during anesthesia for use with anesthesia machines, mechanical ventilators, and/or respiratory function monitors. An algorithm uses end-tidal carbon dioxide ($EtCO_2$), and tidal volume (TV) or peak inspiratory pressure (PIP) to detect exact intubation time. Another algorithm uses respiratory parameters to identify and/or confirm the type of airway device used during mechanical ventilation, and to detect if and when an issue has arisen with use of a specific airway device to provide real-time decision support to attending medical care professionals.

27 Claims, 18 Drawing Sheets

(51) Int. Cl.
  *A61M 16/08* (2006.01)
  *G16H 20/40* (2018.01)
  *G16H 40/63* (2018.01)
  *A61M 16/01* (2006.01)

(52) U.S. Cl.
  CPC ...... *A61M 16/0411* (2014.02); *A61M 16/085* (2014.02); *G16H 20/40* (2018.01); *G16H 40/63* (2018.01); *A61M 2016/003* (2013.01); *A61M 2016/0027* (2013.01); *A61M 2016/0413* (2013.01); *A61M 2205/18* (2013.01); *A61M 2205/3331* (2013.01); *A61M 2205/3553* (2013.01); *A61M 2205/502* (2013.01); *A61M 2205/52* (2013.01); *A61M 2205/60* (2013.01); *A61M 2230/42* (2013.01); *A61M 2240/00* (2013.01)

(58) Field of Classification Search
  CPC ...... A61M 2016/0413; A61M 2205/18; A61M 2205/3331; A61M 2205/3553; A61M 2205/502; A61M 2205/52; A61M 2205/60; A61M 2230/42; A61M 2240/00; G16H 20/40; G16H 40/63
  See application file for complete search history.

(56) References Cited

U.S. PATENT DOCUMENTS

| | | |
|---|---|---|
| 2008/0300464 A1 | 12/2008 | Dhingra et al. |
| 2008/0300475 A1 | 12/2008 | Jaeger et al. |
| 2009/0275805 A1 | 11/2009 | Lane et al. |
| 2011/0190611 A1 | 8/2011 | Rabi |
| 2013/0324872 A1 | 12/2013 | Babaeizadeh et al. |
| 2016/0051780 A1 | 2/2016 | Sherman et al. |

OTHER PUBLICATIONS

International Search Report and Written Opinion for International Application No. PCT/US2017/058252, dated Jan. 3, 2018—8 pages.
Jalali et al., "Automatic Detection of Endotracheal Intubation During the Anesthesia Procedure", Journal of Dynamic Systems, Measurements, and Control, Nov. 2016, vol. 138—8 pages.

| Mode | RR | TV | PIP | EtCO$_2$ |
|------|-------|-------|-------|------|
| VC | Fixed | Fixed | ↑ | ↑ |
| PC | Fixed | Var | Fixed | ↑ |
| VS | Var | Var | ↓ | ↑ |
| PS | Var | Var | ↑ | ↑ |
| VAF | Fixed | Fixed | ↑ | ↑ |

FIG. 6

AUTOMATIC DETECTION OF AIRWAY DEVICE, ENDOTRACHEAL INTUBATION, AND TUBE MISPLACEMENT IN CHILDREN DURING THE ANESTHESIA PROCEDURE

RELATED APPLICATIONS

This application is the U.S. National Phase entry of PCT International Application No. PCT/US2017/058252, filed on 25 Oct. 2017, entitled AUTOMATIC DETECTION OF AIRWAY DEVICE, ENDOTRACHEAL INTUBATION, AND TUBE MISPLACEMENT IN CHILDREN DURING THE ANESTHESIA PROCEDURE, which is related to, and claims the benefit of and priority to, U.S. Provisional Application No. 62/412,508, entitled AUTOMATIC DETECTION OF ENDOTRACHEAL INTUBATION DURING THE ANESTHESIA PROCEDURE, filed on 25 Oct. 2016, the contents of both applications being incorporated herein by reference in their entireties for all purposes.

BACKGROUND OF THE INVENTION

Mechanical ventilation is commonly used in emergency rooms, intensive care units and operating rooms when there is a clinical need to assist or replace spontaneous breathing of the patient. In general, a mechanical ventilator is a machine that generates and regulates the flow of air to the patient's respiratory system. Using the mechanical ventilator, the clinician can control the flow of the air to the patient's airway by setting the different modes of ventilation.

Neonates, infants, and children undergoing major and complex surgeries in the United States undergo general anesthesia and hence are mechanically ventilated for the period of the surgery. Pediatric anesthesiologists must manage children's needs during surgery while documenting their physiologic state in the anesthesia record. Anesthesiologists have traditionally performed this documentation manually on a paper anesthesia record; these records have been shown to contain inaccuracies, particularly when retrospectively recording data such as blood pressure, heart rate, pulse oximetry and ventilation parameters. The cognitive load of monitoring patients while concurrently documenting the anesthesia record can be challenging. The electronic anesthesia record, or Anesthesia Information Management System (AIMS), automates various documentation tasks such as recording patient physiological data, enabling clinicians to focus on caring for the anesthetized patient.

A patient's airway may be supported using various devices that can be classified as noninvasive or invasive ventilation devices. Noninvasive techniques include spontaneous ventilation with a face mask, while invasive techniques include devices such as laryngeal mask airways (LMA) or endotracheal tubes (EU). The anesthesiologist may perform endotracheal (ET) intubation, defined as the placement of an EU in the trachea. Respiratory parameters of the patient, which are continually monitored during surgical procedures and anesthesia, have been shown to differ significantly depending on the type of airway support is used. The types of airway support used display different respiratory patterns. It has been surprisingly found that these patterned differences between the airway types can be used to develop algorithms for identifying and/or confirming the type of airway device used during mechanical ventilation, but also to detect if and when an issue has arisen with use of a specific airway device (e.g., one-lung ventilation during ET intubation, or a misplacement of the EU).

Though ET intubation is one of the fundamental techniques of mechanical ventilation, the EU is often misplaced during the intubation procedure, resulting in an unsuccessful ET intubation. The problem of EU misplacement detection can be divided into different steps: (i) detection of tube placement in the trachea (endotracheal intubation or EU), and (ii) detection of misplacement of the EU.

ET intubation error is an especially complex problem in neonates and younger children due to the very small size of their trachea. Neonates and infants have short airways and accurate positioning of the EU is crucial for adequate mechanical ventilation. Intubation is one of the most important aspects of any surgery since securing the airway is necessary to ensure the patient receives adequate oxygen. Failing to successfully intubate the patient would cause a drop in oxygen saturation, which, if not treated urgently, can result in the patient's death. Oxygen saturation measurements are often made at the patient's fingertip, but this is usually a delayed indicator of poor oxygenation. Such a delay could be very hazardous in neonates and children since their oxygen reserve is very small. Unfortunately, malpositioning of the EU and failure to insert the EU into the trachea is very common in operating rooms and intensive care units. In fact, studies have shown that junior clinicians such as residents and fellows fail to perform intubation correctly in more than 50% of the cases. Another study showed that the success rates for intubation are 37%-51% for residents, 70%-89% for fellows, and 72%-94% for attending physicians. Furthermore, head and neck movements by the patient can induce inadvertent EU movement. This movement can result in inadvertent extubation and endobronchial intubation especially in neonates and infants which in turn causes desaturation and consequently, patient death.

Rapid confirmation of correct ETT placement is clinically crucial because tube malposition is associated with serious adverse outcomes. In an effort to address this problem, various techniques have been applied to enable correct tube placement and optimal positioning of ETT in the trachea. These techniques include: (a) chest radiography, (b) clinical examination (auscultation and bilateral chest rise), (c) measurement of tube length using body parameters, (d) fiber optic techniques, (e) respiratory function monitors, (f) capnography, and (g) ultrasonography. There are also various devices which have been proposed for detection and identification of the endotracheal tube position.

Of all these approaches, the gold standard for ETT tube position detection is chest radiography, which unfortunately has a time delay as the patient needs to be prepared for radiography; it is also of course associated with cost as well as unnecessary radiation exposure to the child. The auscultation of equal and bilateral breath sounds suggests that the ETT is above the carina. However, auscultation as a sole method cannot rule out endobronchial intubation. The measurement of tube length in adults is a reliable method of ETT position detection but in neonates and infants it is not very dependable due to the small trachea size. There are several formulae that have been proposed to achieve correct tube placement. These formulae have a linear correlation with gestational age but have a nonlinear correlation with weight. Furthermore these rules do not apply to nasotracheal intubation. The fiber optic technique is very helpful for tube placement but needs specialized equipment, needs a physician adequately trained in in this technique and is associated with a time delay for the equipment setup. A respiratory function monitor can measure airway gas pressure and flow and also the tidal volume. However, neither gas flow nor airway pressure monitoring can distinguish tube placement in the trachea from one of the main bronchi. The ultrasonography technique needs personnel trained in this technique and specialized equipment, thereby making it a costly and time consuming technique.

There have been many studies on ET intubation. For instance, there are many studies that focus on airway management, correlation between post-surgery complications and difficult airways, detecting intubation through the use of imaging or auscultation techniques, and control of mechanical ventilation. However, despite the clinical importance of ET intubation, algorithmic modeling of ET intubation has not been carried out for either children or adults. Thus there is an urgent clinical need for a decision support system to automatically detect ETT position in the lung and trachea. The desired algorithm would ideally use the data that is already collected by the anesthesia machine such as respiratory rate (RR), tidal volume (TV), peak inspiratory pressure (PIP) and end-tidal carbon dioxide (EtCO2) to detect the ETT position with high accuracy.

SUMMARY OF THE INVENTION

Aspects of the present invention aim to provide algorithmic models of determining, identifying, and/or confirming the airway device used during pediatric surgery, ET intubation during pediatric surgery, and incorrect placement of an ETT during pediatric surgery by using data collected by an anesthesia machine, respiratory function monitor, or mechanical ventilator.

Current physiologic monitors and ventilators provide alarms when individual parameters cross a specific threshold, such as tidal volume below or above a certain value. This results in a variety of alerts, most of which may not indicate clinical problems but can distract the clinicians, producing alert fatigue. Machine learning systems that can accurately identify these changes have the potential to improve clinical monitors and documentation systems by reducing alert fatigue.

A machine-learning data mining algorithm may be incorporated into a system to determine and/or confirm the type of mechanical ventilation airway device used during the anesthesia. The confirmation of the airway device by comparing the output of the algorithm to the clinical decisions of the attending medical providers provides a means by which to determine if the algorithmically derived pattern properly matches the decision by the health care providers, and can provide a basis for determining if problems have arisen during the use of the chosen airway device (e.g., misplacement of an ETT). The algorithm may use respiratory parameters such as respiratory rate (RR), tidal volume (TV), peak inspiratory pressure (PIP), and end-tidal carbon dioxide (EtCO$_2$) to make its determinations and/or confirmations. The confirmation output of the machine-learning data algorithm can also be used in real-time to provide decision support to attending medical care providers.

Other aspects of the present invention aim to provide machine-learning algorithmic models incorporated into systems for detecting incorrect ET placement and/or to distinguish between one-lung and two-lung ventilation. These algorithms may also be incorporated into an anesthesia machine, respiratory function monitor, or mechanical ventilator and may use data already collected by the anesthesia machine, respiratory function monitor, or mechanical ventilator to rapidly and accurately detect incorrect ET placement and alert nearby decision-makers to make appropriate clinical decisions.

An algorithm may be incorporated into a system to detect, predict, and/or estimate a time at which ET intubation is successfully carried out on a patient for clinical charting and decision-making based upon respiratory data measures.

The algorithms and the devices, systems, and methods incorporating the algorithms described herein, could be used in any scenario where the proper mechanical ventilation of a patient is of interest. The algorithms could reside on a clinical device such as an anesthesia machine, respiratory function monitor, or mechanical ventilator as an application, or within another software environment such as a memory. Some, or all, of the respiratory function metrics of interest could be gathered and used in a processing device (e.g., a processor) with the algorithms to produce an output correlated to the ventilation of an individual patient.

Existing methods for detecting ET intubation and/or incorrect ET placement often require specialized training or have lengthy time delays. Moreover, certain methods may need to be combined for accuracy, or have low accuracy rates alone. The inventive devices, systems, methods, and algorithms described herein, however, provide rapid and accurate detection of ET intubation and misplacement useful for clinical decision-makers in a real-time environment.

BRIEF DESCRIPTION OF THE DRAWINGS

The invention is best understood from the following detailed description when read in connection with the accompanying drawings, with like elements having the same reference numerals. Included in the drawings are the following figures:

FIG. 6 is a tabular depiction of the relationship between the mode of mechanical ventilation, mechanical ventilation variables, and intubation in accordance with aspects of the invention;

DETAILED DESCRIPTION OF THE INVENTION

Aspects of the invention provide devices, methods, and systems having one or more algorithms for detecting and confirming the type of airway device used for mechanical ventilation on a patient, and ET intubation and/or misplacement of ETT by using respiratory data measurements of a patient undergoing mechanical ventilation. Anesthesia machines, mechanical ventilators, and/or respiratory function monitors continuously measure respiratory parameters including end-tidal CO$_2$ (EtCO$_2$), tidal volume (TV), peak inspiratory pressure (PIP), and minute ventilation.

A patient's airway may be supported during anesthesia using a number of devices, including mask ventilation (Mask), a laryngeal mask airway (LMA) or an endotracheal tube (ETT). Each of these support devices produce subtle differences in the patient's ventilation parameters. It was surprisingly found that these differences result in patterns that can be used to develop algorithms for determining and confirming the type of airway device used with a patient in real-time, and for identifying potential problems (e.g., ETT misplacement) with the airway device used with a patient if the pattern expected for the actual device used with a patient fails to match the algorithmic determination. Thus, the type and mode of mechanical ventilation can affect the data measurements and algorithmic output. The algorithm(s) described herein incorporate information on the effects on the respiratory data and accommodate differences in mechanical ventilation mode.

Figure 1:
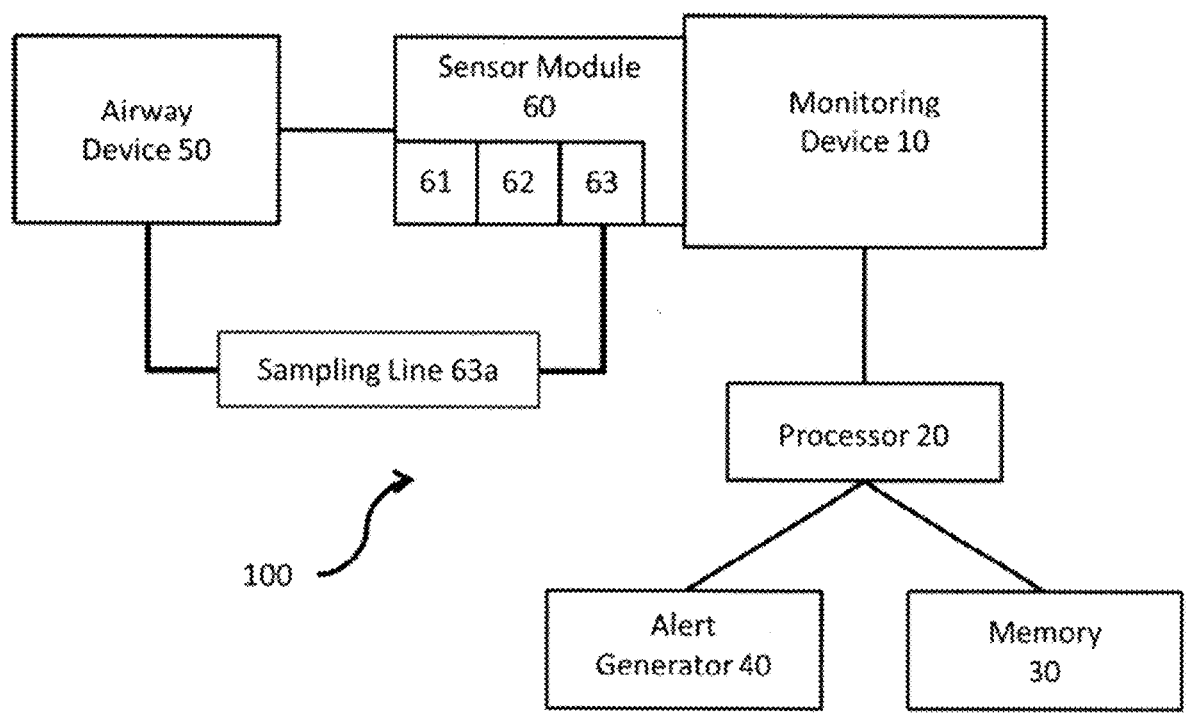
FIG. 1 is a depiction of a system suitable for determining and confirming identity of an airway device used during anesthesia, and for identifying potential problems with the airway device used, in accordance with aspects of the invention.

Overview of Systems and Methods for Determining and Confirming Airway Device Used and for Identifying Potential Problems with the Airway Device Used With reference to the exemplary system 100 embodied in FIG. 1, during anesthesia, a monitoring device 10 (for example, an anesthesia machine, mechanical ventilator, or respiratory function monitor) typically records the patient's ventilation variables/respiratory parameters, including respiratory rate (RR), TV, EtCO2, and PIP. The monitoring device 10 may also record and chart a medical care provider's clinical decision about the type of airway device 50 chosen for use during the patient's anesthesia (for example, the type of airway device may be a mask, LMA, or ETT). The type of airway device 50 (e.g., mask, LMA, or ETT) may change during the anesthesia procedure according to the clinical decisions made, and the monitoring device 10 may record and chart these changes.

There may be one or more sensor modules 60 coupled to or located on or within the anesthesia monitoring device 10 (which may be any of an anesthesia machine, a mechanical ventilator, or a respiratory function monitor), which may operate to capture the different respiratory parameters of the patient during anesthesia. A sensor module 60 may have one or more sensors to capture RR, TV, PIP, or EtCO$_2$. A volume sensor 61 may be used to measure TV. A pressure sensor 62 may be used to measure PIP, and may also be useful for measuring TV. A CO$_2$ sensor 63 associated with the sensor module 60 may be used to measure EtCO$_2$. The CO$_2$ sensor may include a sampling line 63a attached to the airway device 50 used to mechanically ventilate the pediatric patient. The sampling line 63a can be used to pull samples of CO$_2$ released by the respiratory system of the pediatric patient and to deliver the samples to the CO$_2$ sensor 63 for measurement.

A processor 20, which may be coupled to the monitoring device 10, can then use one or more of the recorded respiratory parameters from the monitoring device 10 with a machine-learning data mining algorithm stored in a memory 30 (the memory may be coupled to the monitoring device 10 and/or processor 20) to determine the type of mechanical ventilation airway device 50 generating and regulating the flow of air to the respiratory system of the patient. The machine-learning data mining algorithm is also capable of evolving over time to adapt to changes, which may include changes to the patient population and changes in the practices of medical care professionals. The processor 20 may thereafter compare the determination of the type of airway device to the recorded and charted medical care provider's actual clinical decision regarding the mechanical ventilation airway device 50 chosen for the pediatric patient. The comparison carried out by the processor 20 ascertains whether the processor's algorithmic determination of the airway device's identity is consistent with or matches a respiratory function pattern associated with the actual airway device 50 chosen by the attending medical care provider.

If the processor 20 ascertains that the determination and actual clinical decision are consistent, then the processor 20 may transmit, to the monitoring device 10, the comparison of the determination and decision. The monitoring device 10 may then automatically chart the comparison to record that the algorithm correctly identified the airway device 50 used. The successful identification indicates to health care professionals attending to the patient that the airway device 50 chosen is operating consistent with respiratory patterns typically observed in connection with use of that particular airway device. This aids the health care professionals in making real-time clinical decisions and keeps the health care professionals apprised of the patient's current status.

The processor 20 may also send a confirmation signal to an alert generator 40 if the determination and the clinical decision are consistent. The alert generator 40 may then issue a confirmation message to the attending medical care providers about the confirmation, which may prompt them to carry out further medical decisions based on the consistent airway device identification. Thus, the confirmation provided as a result of the algorithm and comparison provides real-time decision support for the attending medical professionals.

If, however, the comparison by the processor 20 of the algorithmic determination and the actual chosen airway device 50 yields inconsistent results (e.g., the determination identified the airway device as a mask, yet the actually chosen airway device is an ETT), the processor will transmit this information to the monitoring device 10. The monitoring device 10 may automatically record and medically chart the comparison information to provide a record of a potential problem with the chosen airway device 50 during the anesthesia procedure (e.g., if the algorithm determines that a mask is being used, but the actual airway device is an ETT, this could indicate that there is misplacement of the ETT or a problem with the intubation procedure, such as the ET falling into a bronchus). This prompts attending medical care providers to check the airway device 50 being used for any issues that may jeopardize the proper ventilation of the patient. Thus, the algorithm can be used to determine potential misplacement or problems (such as single-lung ventilation with the ET, as opposed to double-lung ventilation).

Additionally, if the processor's comparison yields inconsistent results, the processor will transmit a signal to the same or separate alert generator. The alert generator will receive the signal and issue an alert to the attending medical care providers. Thus, the algorithm can also be used to indicate potential problems in real-time via an alert if the comparison is inconsistent, which allows the medical care providers to make further treatment decisions to determine if there is an issue with the patient's mechanical ventilation.

Figure 2:
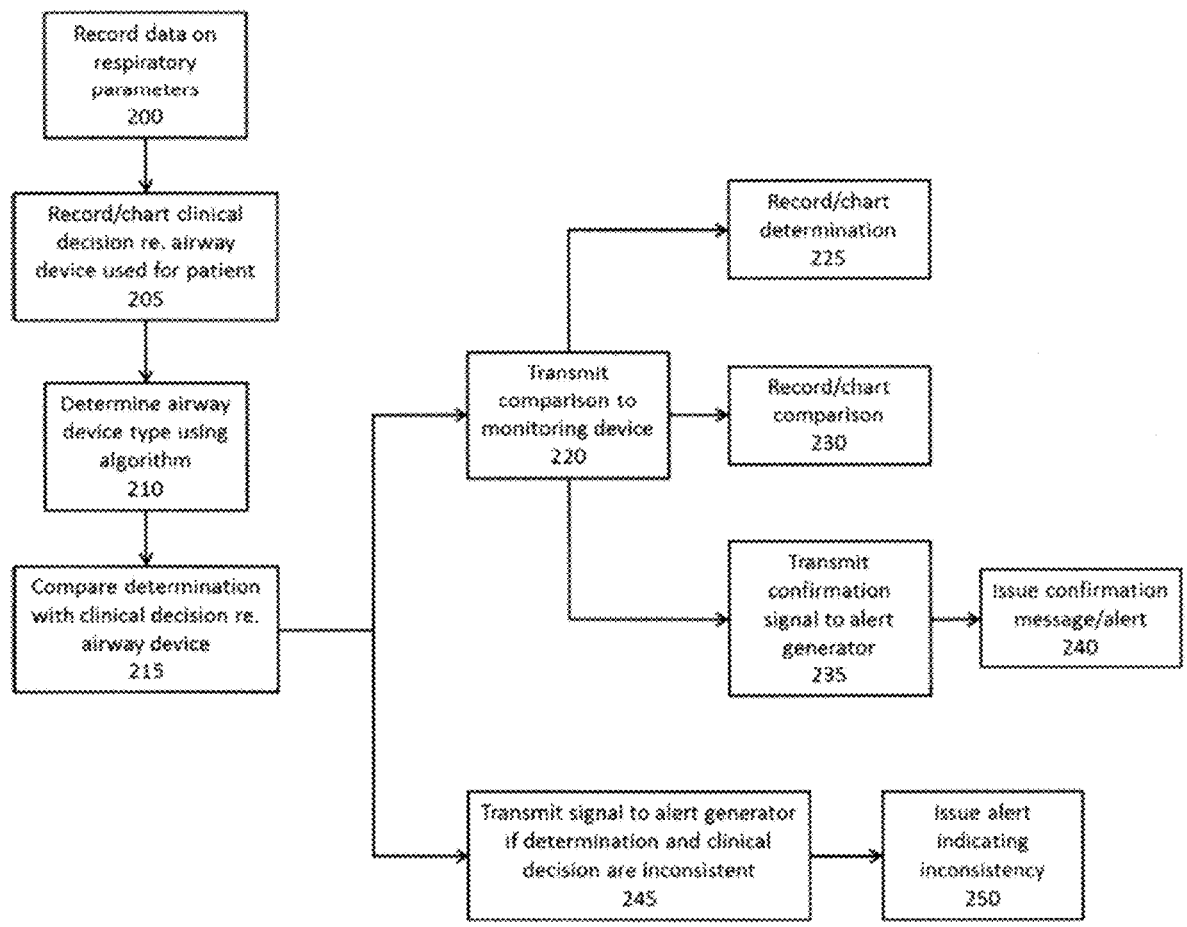
FIG. 2 is a flowchart depicting steps for determining and confirming the airway device used and for identifying potential problems with the airway device used in accordance with aspects of the invention.

FIG. 2 depicts steps for determining and/or confirming the type of airway device used during an anesthesia procedure for a pediatric patient. At step 200, data on respiratory parameters of the patient, which may include respiratory rate (RR), tidal volume (TV), end-tidal CO2 (EtCO2), and peak inspiratory pressure (PIP), may be continually recorded by a monitoring device 10. At step 205, the monitoring device 10 may record and/or medically chart clinical decisions by an attending medical care provider about which mechanical ventilation airway device 50 will be used for the pediatric patient to generate and regulate airflow to the patient's respiratory system.

At step 210, the processor 20 may determine the type of mechanical ventilation airway device generating and regulating the flow of air to the respiratory system of the patient, using the recorded data on the respiratory parameters and a machine-learning data mining algorithm. The algorithm, which is adapted to identify/confirm the type of mechanical ventilation airway device 50 being used during the anesthesia, may be stored in a memory 30. The processor 20 may then at step 215 compare its determination of the type of airway device with the attending medical care provider's clinical decision regarding the airway device 50 actually used to mechanically ventilate the patient. This allows the processor 20 to ascertain whether the determination and the attending provider's decision are consistent; i.e., whether the algorithmic determination and respiratory patterns associated with the specific decision match.

The processor 20 may then transmit the comparison of its determination and the provider's decision to the monitoring device 10 at step 220. The monitoring device 10 may then record and chart the determination made by the processor 20 at step 225. The monitoring device 10 may also record and chart the comparison made by the processor 20 at step 230. At step 235, the processor 20 may also transmit a confirmation signal to an alert generator 40 if the determination and clinical decision are consistent. The alert generator 40 then issues a confirmation message or alert to the attending providers about the consistency at step 240.

If the determination and the decision are inconsistent, e.g., if the algorithm indicates that the airway device 50 is a mask, but the actual clinical decision by the attending medical care provider was to use an ETT, the processor 20 may transmit a signal to the alert generator 40 at step 245. The alert generator will then issue an alert indicating that the determination and decision were inconsistent at step 250.

Machine Learning Systems

Machine learning techniques have increasingly attracted attention from researchers in the biomedical field as a result of their superior performance in comparison with traditional stochastic approaches in prediction, modeling and classification of biomedical systems. The spectrum of machine learning techniques include data mining algorithms and techniques, such as decision trees, support vector machine, and neural networks. These tools facilitate data exploration using data analysis methods with sophisticated algorithms in order to discover unrecognized patterns. Additionally, machine-learning data mining algorithms may be adaptive and capable of evolving over time to accommodate changes. Thus, the algorithms may be specifically "tuned" to the types of data they receive, which may include changes to the patient population and changes in the practices of medical care professionals in the context of different hospitals.

The goal of decision trees (DT) is to use a dataset with known attribute-class combinations for generating a tree structure with a set of rules for classification and prediction of the desired event. The DT consists of a root, internal decision nodes and a set of terminal nodes or leaves, each representing a class. There are two phases in DT induction:

tree building and tree pruning. In tree building phase the goal is to split the data in the way that the divided data-set is more homogenous. To this end, a measure must be defined that quantifies impurity in the data. One of the commonly used criteria is called information gain which is defined by:

$$I(t) = \sum_{i=1}^{M} P(w_i | t) \ln P(w_i | t) \quad [1]$$

where t is the node, M is the number of classes which in binary classification is equal to 2, w is the class, and I represents conditional probability. Boosting or boosted trees is a method of combining hundreds of smaller and weak decision trees to improve accuracy in prediction and classification, and robustness to noise in the data.

Support vector machine (SVM) is a relatively new type of statistical learning machine that provides good generalization capability, which is an important prerogative in the design of any classifier. Generalization capability refers to the capability of a learning machine to perform well with unseen testing data. Support vector machines aim to construct an optimal hyperplane that divide the data with minimum misclassification. The separating hyperplane is represented by equation (wx+b)=0 where, k is the nonlinear kernel, w is set of weights, x is the input vector, and b is bias.

Neural networks (NN) are a type of machine learning classifier that mimic human nervous systems through modeling neurons and their connections. The NN consists of a series of neurons in different layers—input, hidden, and output layers—that are connected together by weights. The neurons apply a function to their input which is called activation function. Multi-layer perceptron neural networks are composed of different layers. The first layer is called the input layer which receives the input to the network; hidden layers are then consequently connected to the input layer and map the input to the higher dimension. The final layer is the output layer which contains the probability of the output. A neural network with a sufficient number of parameters and adequate tuning is able to learn any mathematical transformation.

BT, SVM, and NN machine learning algorithms were applied to respiratory parameters (RR, TV, PIP, and $EtCO_2$) acquired from patients undergoing surgical procedures to identify which of the airway device types were used on a patient, and to distinguish between three types: 1) mask ventilation, 2) LMA, or 3) ETT. The machine learning algorithms can be updated and/or can evolve over time to identify and recognize other airway device types.

Electronic anesthesia records were retrieved from a Clinical Data Warehouse (CDW) consisting of three groups of consecutive patients that received general anesthesia in 2015 with either mask ventilation, LMA or ETT. Patients underwent one of the following procedures: myringotomy, tonsillectomy, adenoidectomy or inguinal hernia repair. Patients undergoing myringotomy procedures typically have a natural airway with spontaneous ventilation that may transition to positive pressure ventilation. Adenoidectomy and tonsillectomy patients have an endotracheal tube (ETT) and may be breathing spontaneously or have positive pressure ventilation. Finally, patients undergoing hernia repairs may have either a laryngeal mask airway (LMA) or an endotracheal tube (ETT) for the procedure.

Figure 3:
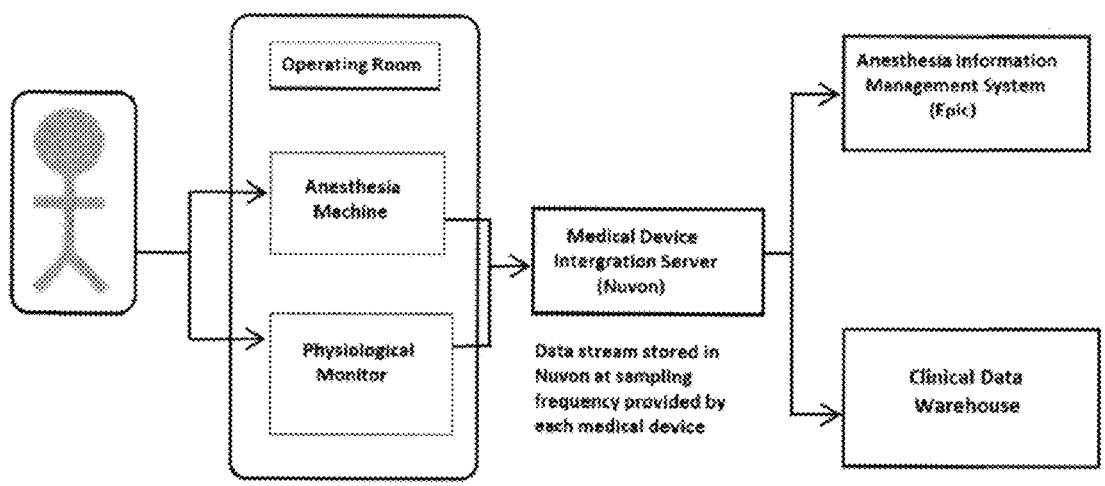
FIG. 3 is a depiction of a system suitable for gathering and storing data related to respiratory parameter measurements from patient undergoing elective surgical procedures in accordance with aspects of the invention.

Clinical documentation consisted of intubation time and airway device used, which are recorded manually by the anesthesia provider, and respiratory parameter measurements were recorded automatically in the AIMS and a clinical data warehouse. Respiratory parameter measurements were recorded from the anesthesia machine in one-minute intervals (FIG. 3). Respiratory parameters including respiratory rate (RR), tidal volume (TV), end-tidal $CO_2$ ($ETCO_2$), and peak inspiratory pressure (PIP) were retrieved. The minute ventilation (MV) was calculated using the following formula: MV=RR & TV.

The following statistical features for each data element per patient were calculated: (1) mean, (2) minimum, (3) maximum, (4) first and (5) third quartile, (6) standard deviation, (7) skewness, (8) kurtosis, (9) median, (10) 10% quantile, (11) 90% quantile, (12) geometric mean, and (13) harmonic mean. Geometric mean is an indicator of central tendency of the variable and is calculated using $$G_m(x) = \sqrt[n]{\prod_{i=1}^{n} x_i}, \quad [2]$$

where x is the physiological measurement and n is the length of the measurement. Harmonic mean is an indicator of rates of changes in the measurement as it is an average of rates. Harmonic mean is calculated using the equation $$H_m(x) = \frac{n}{\sum_{i=1}^{n} \frac{1}{x_i}}. \quad [3]$$

The MATLAB Version R2015B statistical toolbox package was used for extracting the statistical features from the data. Each patient had a total of 65 statistical features. The size of the feature pool was reduced with the mutual information method in order to avoid over-fitting the model. The mutual information method calculates the mutual dependencies of two random variables. The features were ranked based on their mutual information with the outcome based on the following equation:

$$I(X;Y) = \sum_{y \in Y} \sum_{x \in X} p(x,y) \log\left(\frac{p(x,y)}{p(x)p(y)}\right), \quad [4]$$

where X is the feature vector, Y is the output vector, and p(x,y) is joint probability of x and y. The data were randomized and then divided to three sets of 300 patients with 100 in each airway device category per set. The machine learning based classifier was designed with MATLAB to classify the data into two classes (Mask versus airway device: LMA, or ETT). Three different types of machine learning classifiers (BT, SVM, and NN) were evaluated.

The MATLAB neural network package was used to carry on the design of the classifier and the implementation of the neural network machine learning algorithm. To address the bias-variance dilemma in designing the classifier, that is, making the classifier unbiased to the output by increasing the size of the neural network and suppressing the resulting variance, the five layer neural network was trained using a resilient back propagation algorithm 200 times, then calculating the average for connecting weights of the neural network. The neural network was trained using the back propagation of an error. Cross-entropy was used between the neural network estimation and actual output as the loss function to minimize. The cross-entropy for binary classification is defined using $$e_{cross-entropy} = -\frac{1}{N}\sum_{i=1}^{N}[y_i\log\hat{y}_i + (1-y_i)\log(1-\hat{y}_i)], \quad [5]$$

where, $y\varepsilon\{0,1\}$ is the actual output $\hat{y}$ is the estimated output, and N is the batch size. The cross-entropy is proved to be a better loss function for training neural networks as its gradient is not approaching zero when the estimated error approaches zero. An $L^2$ regularization method was used to regularize the weights and biases of network to avoid overfitting. A stochastic gradient descent was used to optimize the loss function. The gradient descent is calculated using:

$$\hat{s} = s - \varepsilon\nabla loss \quad [6]$$

where, $\hat{s}$ is the new estimation of parameter s that minimizes the loss function and s is the learning rate which controls the step length at each iteration of the gradient descent algorithm. The stopping criteria for training each of the neural networks were reaching error rate of less than 0.001.

For the BT method, 200 trees were combined. Each tree was constructed using a different subset sample from the original data. About one-third of the cases were left out of the subset sample and not used in the construction of the $k^{th}$ tree. For building each decision tree, information gain criterion described by equation [1] was used to split the data. Fisher's exact t-test was used to prune redundant branches in the tree. Random forest method was then used to combine the trees. Since the random forest algorithm is built based on subsampling the data, there is no need for cross-validation or a separate test set to get an unbiased estimate of the test set error.

For the SVM method, soft-margin support vector machine (v-SVM) classifier was used. The v-SVM is specifically useful for the cases in which high noise level will cause overlap in the data, which in turn causes a high number of misclassified subjects. Designing the v-SVM will lead to solving the following optimization problem:

$$\text{minimize } W(\alpha) = \frac{1}{2}\sum_{i,j=1}^{m}\alpha_i\alpha_j y_i y_j k(x_i, x_j) \quad [7]$$

$$\text{subject to } 0 \leq \alpha \leq \frac{1}{m}$$

$$\sum_{i=1}^{m}\alpha_i y_i = 0$$

$$\sum_{i=1}^{m}\alpha_i = v$$

where $\alpha$ is the Lagrangian variable, and v is the user-defined soft margin. Sequential minimal optimization (SMO), which is an algorithm for solving the quadratic programming (QP) problem presented by equation [7], was used.

A total of 900 records were retrieved from the CDW (Table 1 below). A training set was used to design the classifiers. Two test data sets were then applied to determine accuracy and generalizability of the classifiers. The feature ranking was only performed on is the training data set to avoid any bias which may be caused by the testing data sets and increase the generalizability of the classifier's performance. The mutual information ranking showed the 20 features [ETCO$_2$ mean, 2nd quantile, geometric mean, 3rd quantile, harmonic mean, 1st quantile, maximum, moment 5; PIP 1st quantile, harmonic mean, geometric mean, mean; TV 1st quantile, harmonic mean, geometric mean; MV harmonic mean, range, 1st quantile, 3rd quantile; and RR range] that represented 90% information required for classification. Among the top 20 ranked features that were included in the classifier, eight are extracted from ETCO$_2$, four from MV, four from PIP, three from TV, and one from RR. The top seven features are extracted from ETCO$_2$.

TABLE 1

Composition of Anesthesia Records Across Three Data Sets

| | | Training Data Set | | | Test Data Set #1 | | | Test Data Set #2 | | |
|---|---|---|---|---|---|---|---|---|---|---|
| | | Mask | LMA | ETT | Mask | LMA | ETT | Mask | LMA | ETT |
| Age (Years) | Mean | 6.7 | 6.7 | 5.9 | 6.1 | 6.8 | 6.1 | 5.5 | 6.7 | 5.4 |
| | Standard Deviation | 4.3 | 3.7 | 3.9 | 4.9 | 3.9 | 4.1 | 4.8 | 3.2 | 3.8 |
| | Minimum | <1 | <1 | <1 | <1 | <1 | <1 | <1 | <1 | <1 |
| | Median | 6 | 5 | 6 | 4 | 6 | 5 | 4 | 6 | 5 |
| | Maximum | 19 | 18 | 21 | 17 | 18 | 18 | 20 | 17 | 17 |
| Sex | Male | 54 | 56 | 71 | 66 | 62 | 64 | 61 | 57 | 77 |
| | Female | 46 | 44 | 29 | 34 | 38 | 36 | 39 | 43 | 23 |
| ASA Status | 1 | 38 | 13 | 60 | 55 | 11 | 54 | 52 | 7 | 58 |
| | 2 | 62 | 87 | 40 | 45 | 89 | 46 | 48 | 93 | 42 |
| Length of Procedure (Minutes) | Mean | 7.6 | 18.8 | 28.2 | 5.4 | 16.9 | 27 | 5.4 | 20.5 | 29.4 |
| | Standard Deviation | 6.4 | 15.5 | 15.2 | 3.9 | 8.5 | 14.3 | 4.5 | 20 | 14 |
| | Minimum | 1 | 0 | 4 | 1 | 5 | 0 | 1 | 5 | 9 |
| | Median | 5 | 17 | 24 | 5 | 15 | 22 | 4 | 18 | 26 |
| | Maximum | 34 | 148 | 85 | 38 | 62 | 78 | 29 | 190 | 102 |
| Length of Anesthesia (Minutes) | Mean | 22.1 | 40.2 | 42.2 | 13.9 | 36.2 | 48.6 | 13.9 | 41.2 | 50.6 |
| | Standard Deviation | 21 | 20.5 | 20.2 | 7.5 | 13.3 | 17.7 | 7.9 | 27.6 | 17.1 |
| | Minimum | 7 | 8 | 7 | 5 | 20 | 21 | 6 | 22 | 25 |
| | Median | 17 | 36.5 | 39 | 12 | 33 | 43 | 12 | 35 | 47 |
| | Maximum | 198 | 137 | 125 | 61 | 104 | 107 | 54 | 224 | 138 |

Mean represents the mean value of the recording. Generally, the mean values for mask ventilation recordings are lower than the mean values for tube and LMA because of higher amount of gas leaks in mask ventilation. Geometric mean as a feature is regularly used in situations in which it is desirable to compare different subjects when there are multiple recording from each subject and each of these recordings have different numeric ranges. Furthermore, geometric mean is often used to mitigate the effect outliers, and since the data collected from intubation is very noisy due to patient movement, leaks, etc., the geometric mean can reduce the effect of noise in the data when comparing different airway management types.

Harmonic mean is typically used in the cases where it is desirable to calculate the average of rates. It is particularly useful for detection of airway management type because it is desirable to understand the rate of changes in the anesthesia machine measurements. Mask ventilation has typically more sudden changes in the measurement because of gas leaks. Hence, the harmonic means of anesthesia machine measurements such as respiratory rate are usually higher for mask ventilation in comparison with endotracheal tube (ETT) or laryngeal mask airway (LMA) ventilation techniques. Quartiles, including first, second, and third quartiles, and statistical moments are a way to determine the probability distribution functions of the measurements to be able to better classify them. Machine learning in general tries to learn the probability density function that generates the input to the classifier (anesthesia machine measurements) to be able to distinguish different classes (mask vs laryngeal mask airway or endotracheal tube).

The NN classifier performed better than the BT and SVM classifiers based on the test data sets. The sensitivity, specificity, and accuracy for each airway device NN are 97.5%, 96.3%, and 95.8%, respectively. In contrast, the sensitivity, specificity, and accuracy are 89.1%, 92.3%, and 88.3% for SVM and 93.8%, 92.1%, and 91.4% for BT respectively. Table 2 (below) depicts the aggregate performance of the machine learning classifiers on the test data sets based on correct identification of the airway device used (mask ventilation, LMA, or ETT). There were 10 false negative cases and nine false positive cases.

TABLE 2

Comparison of the classification performance between the three machine-learning algorithms
Comparison of the accuracy between the 3 machine learning classifiers.

|  | Neural Network | Support Vector Machine | Boosted trees |
| --- | --- | --- | --- |
| Sensitivity | 97.5% | 89.1% | 93.8% |
| Specificity | 96.3% | 92.3% | 92.1% |
| Accuracy | 95.8% | 88.3% | 91.4% |

A 5-fold cross validation was performed on the data, in which the data was randomly divided into 5 groups of 180 patients, and the algorithm was then trained using 4 groups. The algorithm was then tested using the group excluded from training. This process was repeated 5 times, and the results are shown in Table 3 (below).

TABLE 3

Neural network 5-fold cross validation

| Group Number | Sensitivity | Specificity | Accuracy |
| --- | --- | --- | --- |
| 1 | 97.1 | 96.6 | 95.8 |
| 2 | 95.8 | 96.1 | 95.2 |
| 3 | 98.3 | 96.7 | 95.4 |
| 4 | 96.7 | 97.2 | 95.9 |
| 5 | 97.4 | 95.9 | 95.1 |

Figures 4A, 4B:
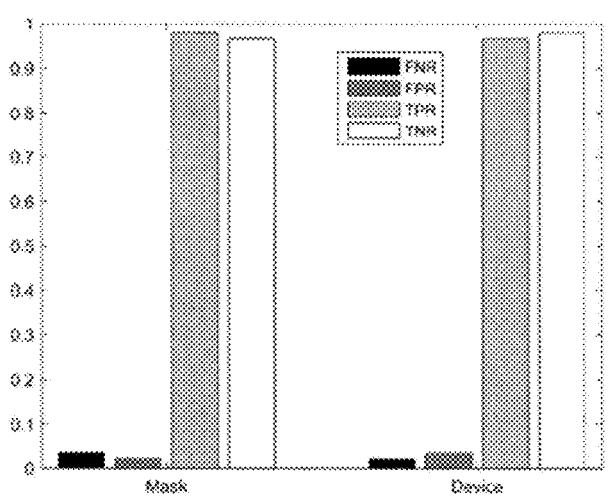
FIG. 4A is a truth table depicting classification results obtained for the neural network algorithm training data set in accordance with aspects of the invention.
FIG. 4B is a graph depicting data obtained for the neural network algorithm training data set in accordance with aspects of the invention.
Figure 4C:
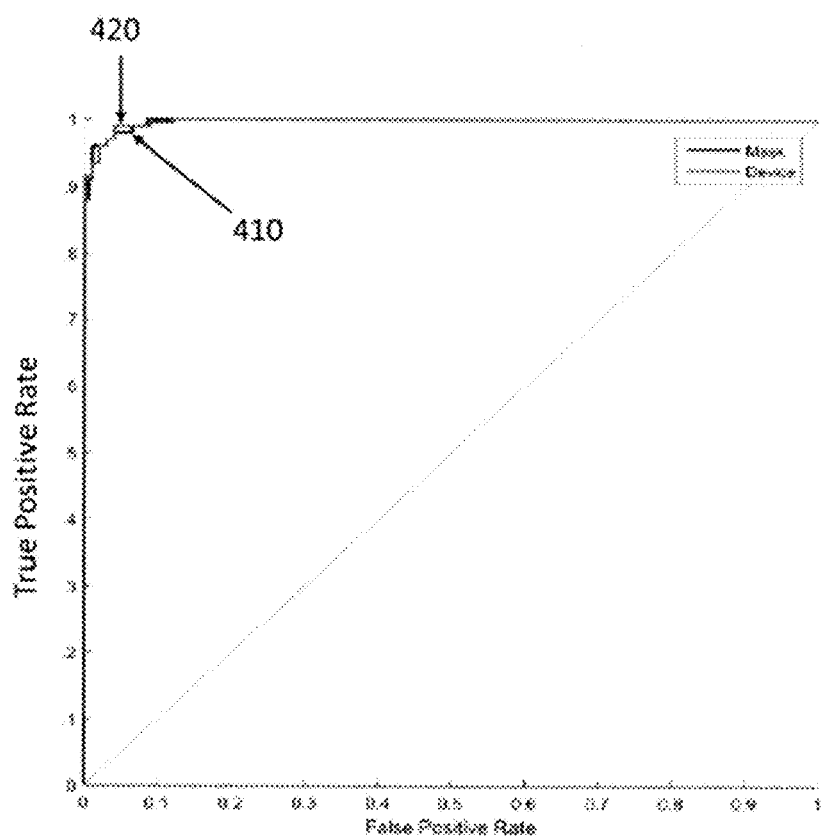
FIG. 4C is a graph depicting the receiver operating characteristic curve (ROC) for the neural network algorithm training data set plotting true positive rate against false positive rate of the neural network algorithm in accordance with aspects of the invention.

The confusion rates showing the false negative, false positive, true positive and true negative rates for the neural network classifier for validation/training and test datasets are shown in FIGS. 4A-4C (validation/training datasets) and 5A-5C (test datasets). The neural network classifier performs consistently in the test data sets and works best in distinguishing patients with noninvasive ventilation via mask from those that have invasive ventilation with an airway device (laryngeal mask airway or endotracheal tube).

FIG. 4A presents a truth table for the validation/training dataset for the neural network classifier. The validation/training data includes 100 cases in which a face mask was used, and 200 cases in which an airway device (ETT, LMA) was used. The truth table depicts that the neural network classifier was able to correctly classify the device used with the patient in 93 face mask cases and 198 airway device cases.

FIG. 4B is a graph depicting the true positive rate (TPR), the true negative rate (TNR), the false positive rate (FPR), and the false negative rate (FNR) of the neural network classifier as applied to the validation/training dataset. FIG. 4C depicts the receiver operating characteristic curve (ROC) for the neural network algorithm as applied to the validation/training dataset. This plots the true positive rate (TPR) against the false positive rate (FPR) of the neural network classifier for the validation/training data to illustrate the performance of the algorithm for identification of both face mask cases (curve 410) and airway device cases (curve 420).

Figures 5A, 5B:
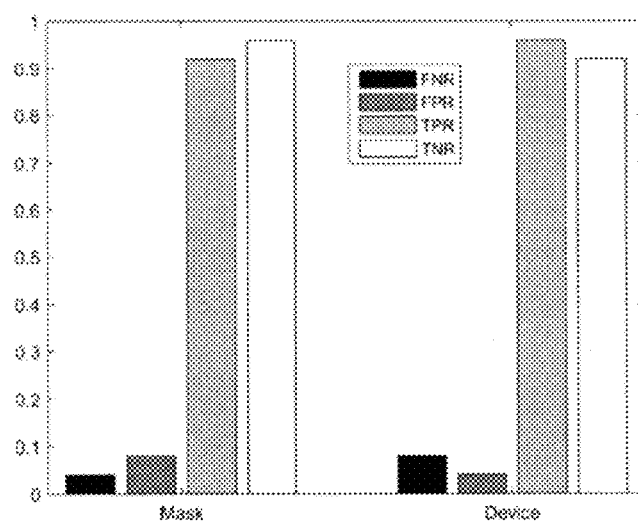
FIG. 5A is a truth table depicting classification results obtained for the neural network algorithm test data set in accordance with aspects of the invention.
FIG. 5B is a graph depicting data obtained for the neural network algorithm test data set in accordance with aspects of the invention.

FIG. 5A presents a truth table for the test dataset for the neural network classifier. The test data includes 100 cases in which a face mask was used, and 200 cases in which an airway device (ETT, LMA) was used. The truth table depicts that the neural network classifier was able to correctly classify the device used with the patient in 92 face mask cases and 192 airway device cases.

Figure 5C:
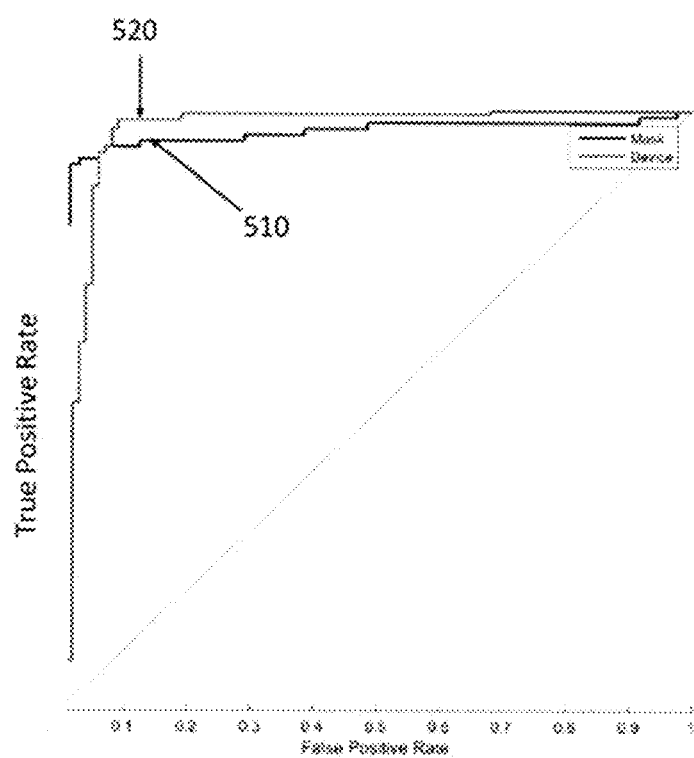
FIG. 5C is a graph depicting the receiver operating characteristic cure (ROC) for the neural network algorithm test data set plotting true positive rate against false positive rate of the neural network algorithm in accordance with aspects of the invention.

FIG. 5B is a graph depicting the true positive rate (TPR), the true negative rate (TNR), the false positive rate (FPR), and the false negative rate (FNR) of the neural network classifier as applied to the test dataset. FIG. 5C depicts the receiver operating characteristic curve (ROC) for the neural network algorithm as applied to the test dataset. This plots the true positive rate (TPR) against the false positive rate (FPR) of the neural network classifier for the test data to illustrate the performance of the algorithm for identification of both face mask cases (curve 510) and airway device cases (curve 520).

Detection of ET Intubation

Modes of Mechanical Ventilation

In general, the mode of mechanical ventilation describes the primary method of inspiratory assistance by an anesthesia machine or mechanical ventilator. Specifically, these machines may control generation of the volume of air (tidal volume (TV)) or the pressure of air (peak inspiratory pressure (PIP)). A clinician will determine a pre-set volume or pressure, and then the machine or ventilator generates a flow of gas into the lungs until, respectively, the predetermined volume or pressure has been delivered. Mechanical breaths or respiratory rates may be controlled (meaning that the ventilator is active and the patient is passive), or be assisted (meaning that the patient initiates the breath and may or may not participate in the breath). A monitoring device (which may be the anesthesia machine or the mechanical ventilator itself, or a separate respiratory function monitor) records respiratory parameters of the patient throughout the anesthesia (including TV, RR, PIP, and $EtCO_2$).

The main impact of the mode of mechanical ventilation is on the mechanical ventilation related variables and respiratory parameters. The morphology of most of the ventilation variables/parameters such as RR, PIP, positive end expiratory pressure (PEEP), and TV depends heavily on the ventilator mode and settings. For instance, breathing could be spontaneous or under ventilator control. Moreover, controlled forms of ventilation could deliver either a preset peak inspiratory pressure or tidal volume. FIG. 6 shows the relationship between the mode of mechanical ventilation, mechanical ventilation variables, and intubation. FIG. 6 shows how different ventilation variables are affected by the mode of ventilation during anesthesia, and especially intubation. "VC" is volume control, "PC" is pressure control, "VS" is volume support, "PS" is pressure support, and "VAF" is variable auto flow. The symbol indicates increase in the variable during the intubation while indicates decrease in the value. FIG. 6 also reveals a surprising fact: unlike other mechanical ventilation variables, the changes in the $EtCO_2$ pattern remain the same regardless of the mode of ventilation. Thus, $EtCO_2$ was used as the main variable to develop the algorithm(s).

Sensor modules coupled to or located on or within the anesthesia monitoring device (which may be any of an anesthesia machine, a mechanical ventilator, or a respiratory function monitor) may operate to capture different respiratory parameters of the patient during anesthesia. A sensor module may have one or more sensors to capture respiratory rate, TV, PIP, or $EtCO_2$. A volume sensor may be used to measure TV. A pressure sensor may be used to measure PIP, and may also be useful for measuring TV. A $CO_2$ sensor associated with the sensor module may be used to measure $EtCO_2$. The $CO_2$ sensor may include a sampling line attached to a ventilation mask or ET used to mechanically ventilate the pediatric patient. The sampling line can be used to pull samples of $CO_2$ released by the respiratory system of the pediatric patient and to deliver the samples to the $CO_2$ sensor for measurement.

$EtCO_2$ Pattern During Intubation

Induced changes in the end-tidal Carbon dioxide volume (EtCO2) were explored as a function of different events that happen during anesthesia, and particularly during the endotracheal (ET) intubation procedure. $EtCO_2$ is defined as the partial pressure or maximum concentration of $CO_2$ at the end of exhalation process, for which the normal values are 35-40 mmHg. In general, during anesthesia with mechanical ventilation, the anesthesiologist starts with mask ventilation. Mechanical ventilation recordings of respiratory data from the mask generally have a high variation due to the fact that imperfect mask sealing often results in gas leakage, which causes noisy and unreliable recordings. In some surgeries, the intravenous (IV) line is placed to allow for the possibility of injecting more anesthetics (if needed) to get the patient to the desired level of anesthesia. The fresh gas flow is then typically turned off immediately prior to tube placement. This will cause a sharp drop in the values of the recordings. However, residual gas in the ventilation circuit will still contribute to recordings.

In the next step, the ETT is inserted in the trachea and thereafter connected to the ventilation circuit. Next, one of the anesthesia team members hand-ventilates the patient to confirm chest rise and capnography ($EtCO_2$) recordings. At this point, spikes in $EtCO_2$ and pressure recordings by the monitoring device will be observed due to the high influx of air. After confirmation of the tube placement the anesthesiologist will assess the tube depth for catching any tube misplacement that may occur. After assessment of leakage and possible cuff inflation the attending physician may disconnect the tube from the circuit to tape it for better stability. At this point, the patient is ready for surgery. After tube placement, variation in the recordings may still be observed as a result of possible leakage in the circuit. However, the magnitudes of these variations are usually smaller than the variations seen in the mask ventilation phase.

Figure 7A:
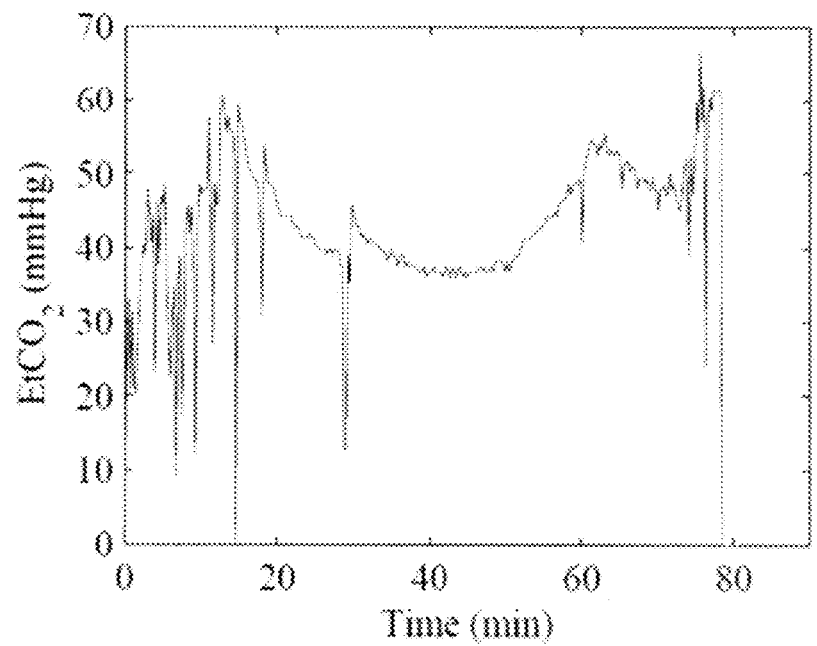
FIG. 7A is a graph depicting actual EtCO$_2$ data collected during a tonsillectomy and adenoidectomy surgery on an eight-year old child in accordance with aspects of the invention.
Figure 7B:
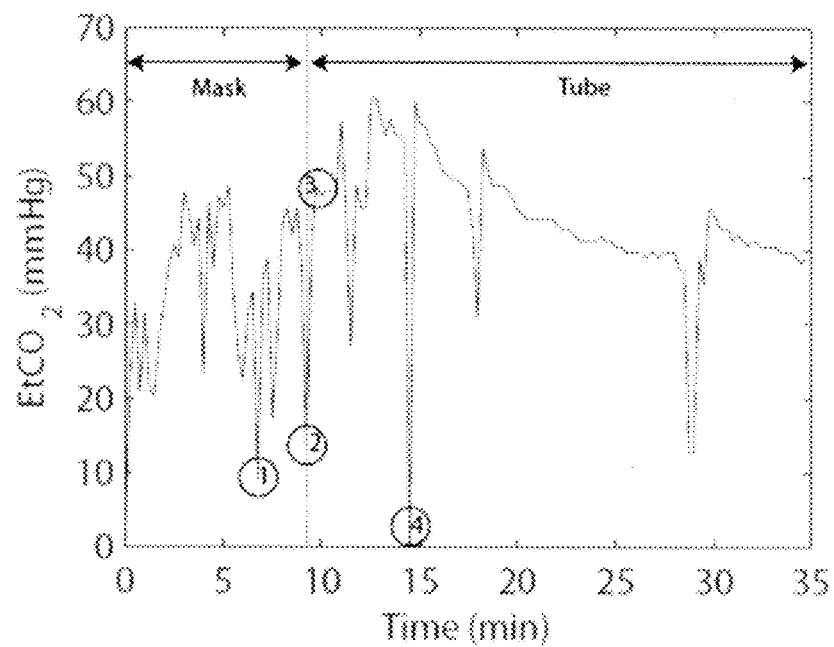
FIG. 7B is a graph depicting a sampling of events during an endotracheal (ET) intubation event in accordance with aspects of the invention.

FIGS. 7A and 7B show an example of real data collected at the Children's Hospital of Philadelphia during Tonsillectomy and Adenoidectomy (T&A) surgery on an eight-year old male child. FIG. 7B shows the magnified section from the beginning until approximately ten minutes after the intubation, and has a sampling of events during the intubation labeled (i.e., 1 is the turning off of the fresh gas flow, 2 depicts the time of intubation, 3 depicts hand ventilation of the patient, and 4 is the taping of the ETT). FIG. 7B exemplifies the complexity of the task of detecting the intubation time. As explained earlier, many steps occur during the anesthesia as part of preparing the patient for surgery, which affect the parametric data that is collected from the anesthesia machine, respiratory function monitor, or mechanical ventilator. Additionally, not all of these steps happen during all types of surgeries and even all cases of one type of surgery. For example, taping of the tube after intubation mainly occurs in T&A surgery.

Algorithmic Design

An algorithmic model for the detection of ET intubation time may be stored in a memory coupled to a processor capable of using the ET intubation algorithm to determine the ET intubation time. With respect to this algorithmic model for detecting ET intubation, the main changes in $EtCO_2$ during anesthesia can be summarized as follows: (i) before the intubation, recordings have smaller magnitudes and are noisier, and (ii) after intubation, recording magnitudes are higher and are less noisy. In mathematical terms, mask ventilation recordings (before intubation) have low mean, high frequency and high variance, while the ETT recordings have higher mean, low frequency and small variance. Three features are defined to detect the intubation time based on these observations from the trends in the data. These features are calculated for a moving window of the signal. The extracted features from the data are (i) mean, (ii) variance, and (iii) the wavelet coefficient's variation index.

The biomedical signals are often nonstationary, i.e., their frequency content varies over time, since the patient's state of health typically changes dynamically. This can also be inferred from FIGS. 7A and 7B as changes in frequency, mean, etc. of the $EtCO_2$ signal can be observed over time. Wavelet transform is generally considered to be the optimal way to analyze nonstationary signals. The continuous wavelet transform possesses the ability to construct a time-frequency representation of a signal that offers very good time and frequency localization. Thus, continuous wavelet transforms (CWT) were used to analyze the nonstationary behavior of the EtCO$_2$ signal.

The CWT of a signal x(t) is defined by Eq. [8], and given here for completeness:

$$C(a, b) = \frac{1}{\sqrt{|a|}} \int_{-\infty}^{\infty} x(t)\psi^*\left(\frac{t-b}{a}\right) dt \quad [8]$$

where, a is the time scale, b is the transitional value, and $\psi^*$ is the complex conjugate of the mother wavelet function $\psi$. However, there is no standard method to choose a mother wavelet function for a specific problem. The Morlet function (defined by Eq. [9]) was therefore used as a mother wavelet function because this is often the function of choice for nonstationary signal behavior in the literature.

$$\psi_k(t) = C_k \pi^{-0.25} e^{-0.5t^2}(e^{jkt} - e^{-0.5k^2}) \quad [9]$$

where k allows for a trade-off between time and frequency resolutions. The variation index of the wavelet coefficient is defined by Eq. [10] as:

$$C_v = \frac{\sigma^2}{\mu^2} \quad [10]$$

where $\sigma$ and $\mu$ are the standard deviation and mean values, respectively, of the CWT coefficients.

The processor, which may be part of the monitoring device or coupled to the monitoring device, may use the algorithm stored in the memory to detect exact ET intubation time. The features for a moving window of the signal are calculated by the processor, and then the trends of these features are analyzed by the processor before and after the endotracheal intubation. The results of the analysis are as follows:

1. Mean of the windowed signal: low during the mask ventilation, jumps during the intubation, high after intubation.
2. Variance of the windowed signal: increases during the mask ventilation, reaches the maximum during the intubation, and decreases after intubation.
3. Variation index of wavelet coefficients: increases during the mask ventilation, reaches the maximum during the intubation, and decreases after intubation.

Based on these results, possible candidates for the intubation time are flagged or identified when each of these features are calculated and analyzed. The high level description of the designed algorithm is presented below.

Figure 8:
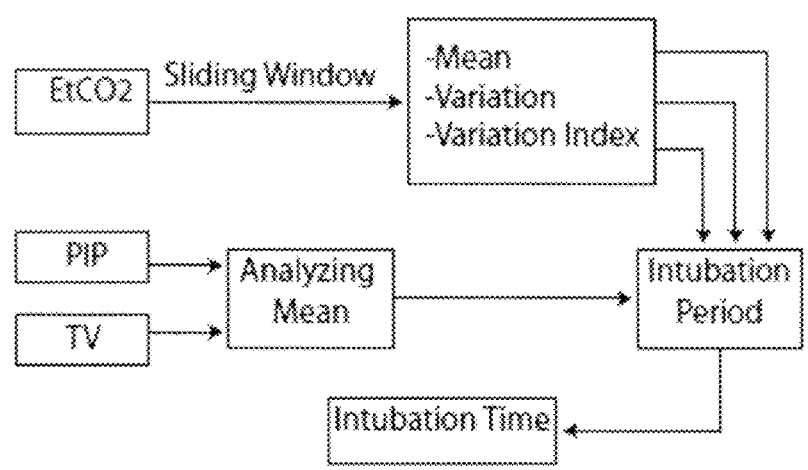
FIG. 8 is a schematic overview of the algorithm for detecting the time of ET intubation in accordance with aspects of the invention.

High Level Description of the Designed Algorithm for Detecting ET Intubation
 1. EtCO$_2$ data is streaming
 2. Start the window from N$^{th}$ recording
 3. Calculate the following three features for window length L:
  (a) Mean
  (b) Variance
  (c) Variation Index of wavelet features
 4. Flag intubation time for each feature based on the analysis
 5. Find the intubation based on the three flagged/identified candidate times To find and confirm the exact intubation time based on the three flagged candidate intubation times, tidal volume (TV) or peak inspiratory pressure (PIP) is used. TV will be used to confirm the intubation time if the mode of ventilation is volume control (VC), volume auto flow (VAF), or volume support (VS). PIP will be used to confirm intubation time if the mode of ventilation is pressure support (PS) or pressure control (PC). The mean of TV or PIP is calculated before and after each of the three flagged times. The time that correlates with the highest jump in the mean for the appropriate variable (TV or PIP) is then flagged as the intubation time. This addition to the algorithm for detection of ET intubation ensures its robustness as it provides another layer for checking for and confirming the intubation time. FIG. 8 represents the schematic design of the developed algorithm. A sliding window with length L moves through the start to the N$^{th}$ recording of EtCO$_2$. At each increment, the three features (mean, variance, and variation index of wavelet coefficients) are calculated from the data. Based on each of these features, a time instant is flagged as the intubation time. The exact intubation time is then detected based on the information from the PIP and TV data. N and L are the design parameters of the algorithm which are chosen and tuned based on the collected data.

High Level Mathematical Description of the Designed Algorithm for Detecting ET Intubation
 1. i=1, j=1, k=1, $C^0_{vi}$=0, $\Delta C_{vi}$=0, $\Delta C_m$=0, $\Delta C_v$=0,
 2. initialize N & M & V
 3. P=M=N, V=N
 4. while $\Delta C_{vi} > \varepsilon_1$ (starts with wavelet variation index)
  (a) calculate CWT coefficients at scale 50 (x),
  (b) s={x(1), x(2), x(N)}
  (c) calculate $\Delta C'_{vi}$,
  (d) calculate $\Delta C_{vi} = C'_{vi} - C_{vi}^{i-1}$,
  (e) P=P+1, i=i+1
 5. end while
 6. while $\Delta C_m > \varepsilon_2$
  (a) calculate mean of the window ($m_j$),
  (b) calculate $\Delta C_v = m_j - m_{j-1}$,
  (c) M=M+1, j=j+1
 7. end while
 8. while $\Delta C_v > \varepsilon_3$
  (a) calculate variance of the window ($v_k$),
  (b) calculate $\Delta C_m = v_k - v_{k-1}$,
  (c) V=V+1, k=k+1
 9. end while
 10. return P, M, and V
 11. $\rho_P$=mean(pip(1:P)), $\rho_M$=mean(pip(1:M)), $\rho_V$=mean(pip(1:V))
 12. tv$_P$=mean(tv(1:P)), tv$_M$=mean(tv(1:M)), tv$_V$=mean(tv(1:V))
 13. $\rho_{P+1}$=pip(P+1), $\rho_{M+1}$=pip(M+1), $\rho_{V+1}$=pip(V+1)
 14. tv$_{P+1}$=tv(P+1), tv$_{M+1}$=tv(M+1), tv$_{V+1}$=tv(V+1)
 15. $\Delta \rho_P = \rho_{P+1} - \rho_P$, $\Delta \rho_M = \rho_{M+1} - \rho_M$, $\Delta \rho_V = \rho_{V+1} - \rho_V$,
 16. Intubation time=index max ($\Delta \rho_P$, $\Delta \rho_M$, $\Delta \rho_V$)

Results of Designed Algorithm for Detecting ET Intubation

To evaluate the performance of the designed algorithm for detecting ET intubation in children, patient respiratory data collected from inpatient operating rooms over four years was used. The collected dataset consists of 600 de-identified patients varying in age between 1 and 18 years. The dataset consists of the relevant anesthesia machine variables (EtCO$_2$, PIP, and TV) with a sampling rate of 15 seconds. Additionally, the data consists of demographics of the patients such as gender, type of surgery, weight, patient position during the surgery, etc. Though this parametric data was collected at a relatively low sampling rate, studies have shown that parametric data can be successfully used in the field of healthcare diagnostics. For instance, Del Pozo et. al. mathematically proved that the minimum sampling rate required to develop a parametric representation of a blood pressure signal is 12 samples per day.

The design parameters of the algorithm used are listed in Table 4 (below). This table shows the design parameters and accuracy of the algorithm based on the changes in these parameters. From this table it is clear that the algorithm is most sensitive to the choice of $\varepsilon_3$ with 7% variation in the accuracy of the algorithm on changing this parameter. Based on the sensitivity analysis in this table, the following values for the parameters were used: L=30, $\varepsilon_1$=0.05, $\varepsilon_2$=5, and $\varepsilon_3$=1.

TABLE 4

Design parameters of the algorithm

| Parameter | Value | Accuracy % |
|---|---|---|
| L | 20 | 90% |
|  | 25 | 90% |
|  | 30 | 96% |
|  | 35 | 91% |
|  | 40 | 91% |
| $\varepsilon_1$ | 0.045 | 92% |
|  | 0.05 | 96% |
|  | 0.055 | 93% |
| $\varepsilon_2$ | 4.5 | 90% |
|  | 5 | 96% |
|  | 5.5 | 92% |
| $\varepsilon_3$ | 0.9 | 89% |
|  | 1 | 96% |
|  | 1.1 | 92% |

Figure 9A:
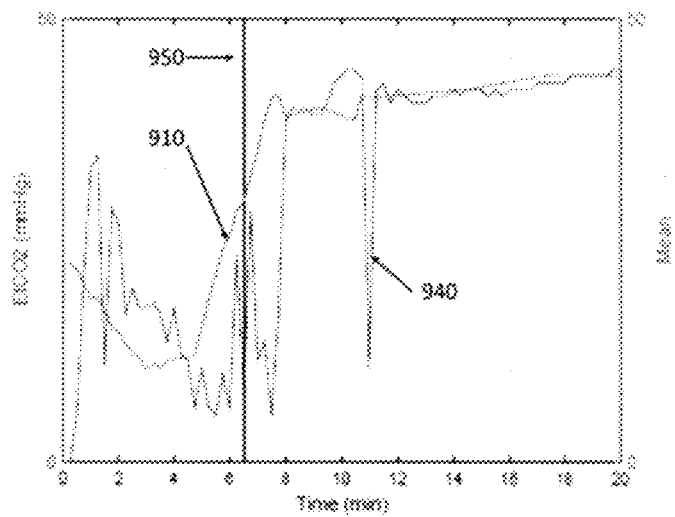
FIG. 9A is a graph depicting the mean calculated for a sample case using the algorithm in accordance with aspects of the invention.
Figure 9B:
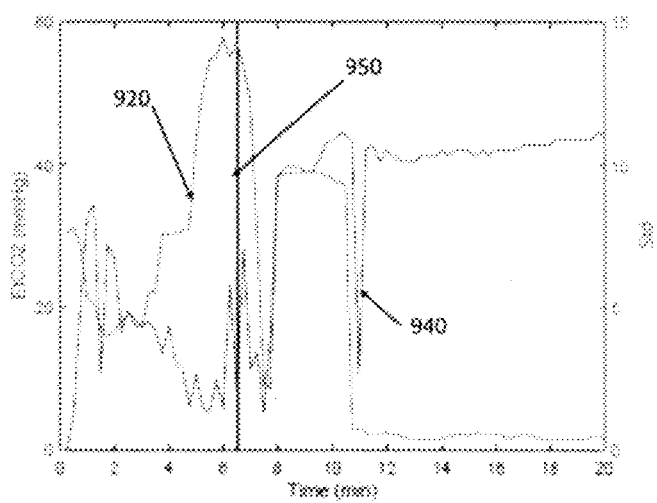
FIG. 9B is a graph depicting the variance calculated for a sample case using the algorithm in accordance with aspects of the invention.
Figure 9C:
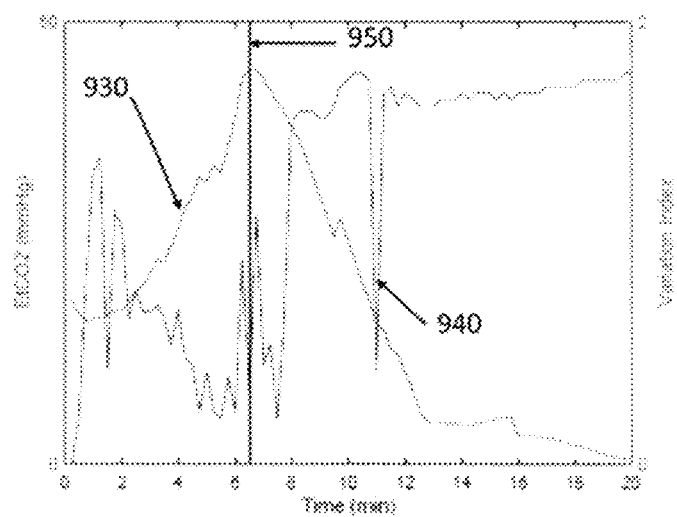
FIG. 9C is a graph depicting the variation index calculated for a sample case using the algorithm in accordance with aspects of the invention.
Figure 10A:
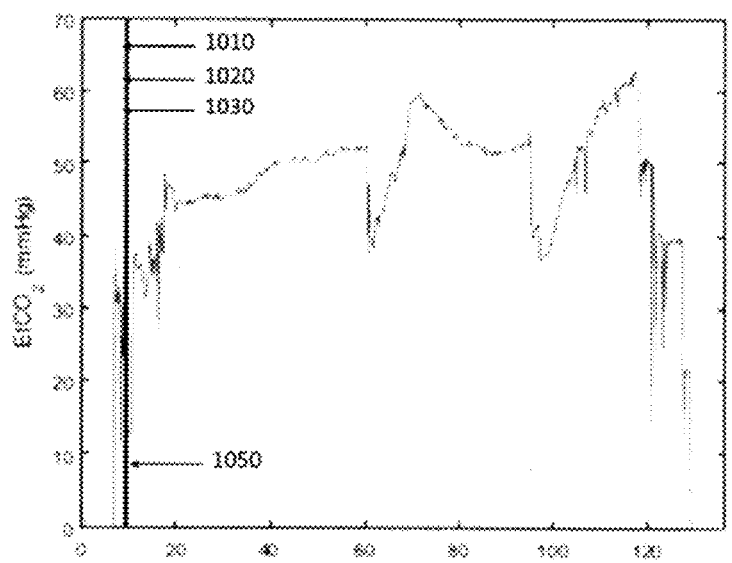
FIG. 10A is a graph depicting the ET intubation time flagged by all the features (variation index, mean, and variance) and the exact ET intubation time based on TV or PIP data in accordance with aspects of the invention.
Figure 10B:
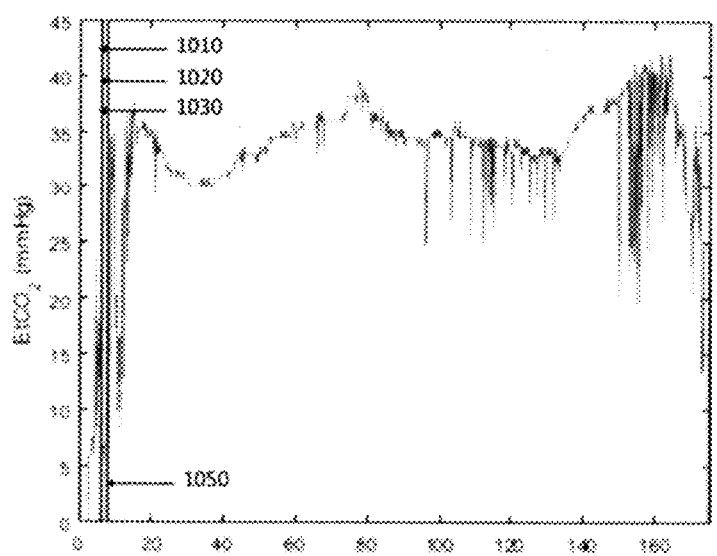
FIG. 10B is a graph depicting the ET intubation time flagged by all the features (variation index, mean, and variance) and the exact ET intubation time based on TV or PIP data in accordance with aspects of the invention.
Figure 10C:
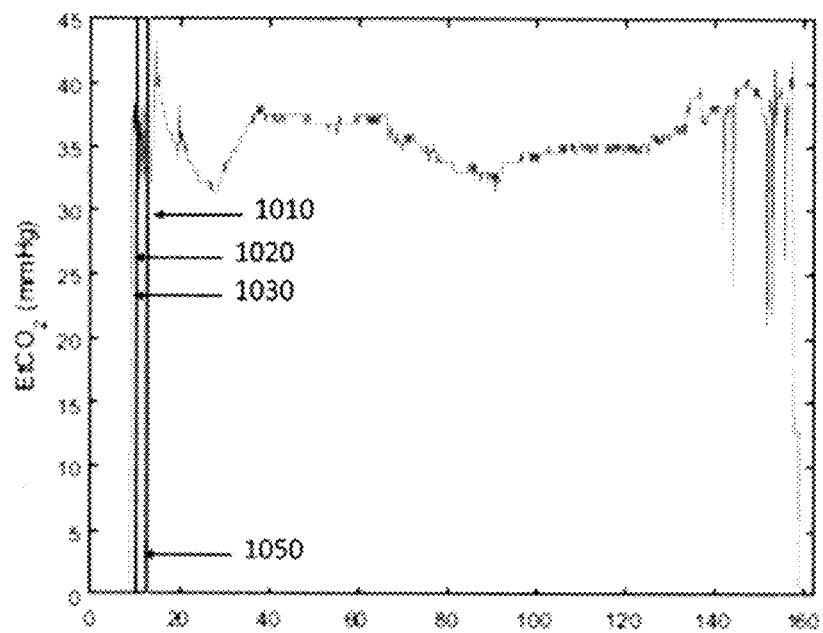
FIG. 10C is a graph depicting the ET intubation time flagged by all the features (variation index, mean, and variance) and the exact ET intubation time based on TV or PIP data in accordance with aspects of the invention.
Figure 10D:
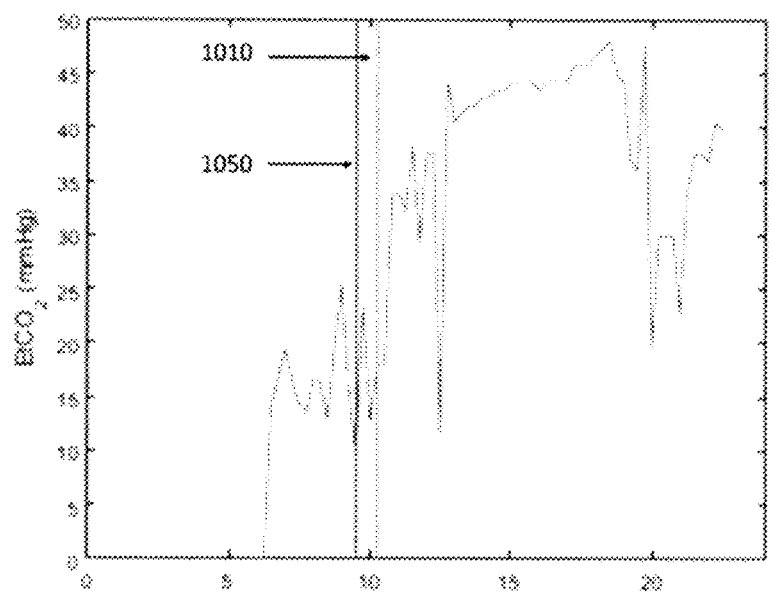
FIG. 10D is a graph depicting the ET intubation time flagged by all the features (variation index, mean, and variance) and the exact ET intubation time based on TV or PIP data in accordance with aspects of the invention.
Figure 10E:
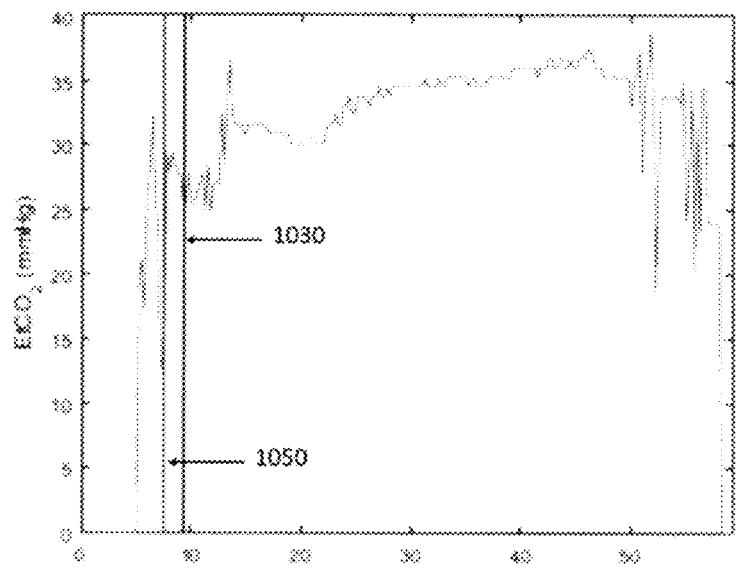
FIG. 10E is a graph depicting the ET intubation time flagged by all the features (variation index, mean, and variance) and the exact ET intubation time based on TV or PIP data in accordance with aspects of the invention.
Figure 10F:
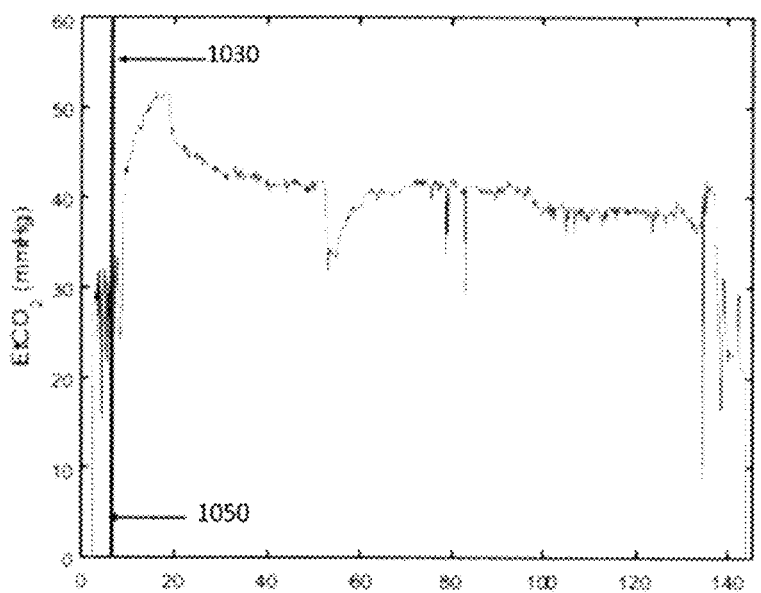
FIG. 10F is a graph depicting the ET intubation time flagged by all the features (variation index, mean, and variance) and the exact ET intubation time based on TV or PIP data in accordance with aspects of the invention.

Choice of N takes into account the fact that most of the cases begin with artifacts caused by a variety of reasons as the clinical team would be preparing the room or the patient, and going through many other preparatory procedures. The collected data showed is that it usually takes 10 minutes from start of the data collection until endotracheal intubation. As a result, N was chosen to be half of this; i.e., 5 minutes, or 20 samples. With this strategy, it was possible to control the robustness of the algorithm. FIGS. 9A, 9B, and 9C show, respectively, plots of mean 910, variance 920, and variation index 930 with a plot of $EtCO_2$ 940 for a sample case. In this particular case, all features agree and point to the same spot as the intubation time 950.

For a variety of reasons, such as disconnection of anesthesia machine, the patient data often contains wrong or missing measurements. The algorithm replaces the missing data with the last known data for the corresponding period.

FIGS. 10A-10F show the results on intubation detection time in some sample cases. The plots show the intubation time flagged by all the features (variation index, mean, and variance) and the exact intubation time based on TV or PIP data (the so-called "ground truth"). Line 1010, line 1020, and line 1030 represent the flagged intubation times based on the variation index, the mean, and the variance respectively. Line 1050 represents the exact intubation time, the "ground truth," as identified by either the TV or PIP data. As plots show, in many cases, the flagged time by different features actually overlap with each other. In these cases, the ET intubation algorithm was capable of detecting the intubation time precisely.

As stated above, data from 600 patients was used. The results show that the algorithm could precisely detect intubation time in 547 of those cases. In 32 cases, it could detect intubation time within three samples of the actual time, which is still clinically reliable. The algorithm failed to converge and did not flag intubation in only four cases. In other words, results show that the algorithm is capable of exactly detecting intubation in 91% of cases, and it can correctly detect intubation time within one minute in 96% of cases.

Figure 11A:
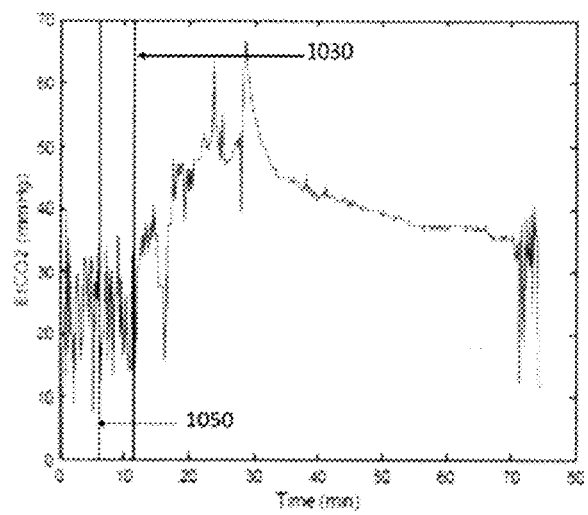
FIG. 11A is a graph depicting an instance in which the algorithm detects the ET intubation five minutes earlier than its actual time, in accordance with aspects of the invention.
Figure 11B:
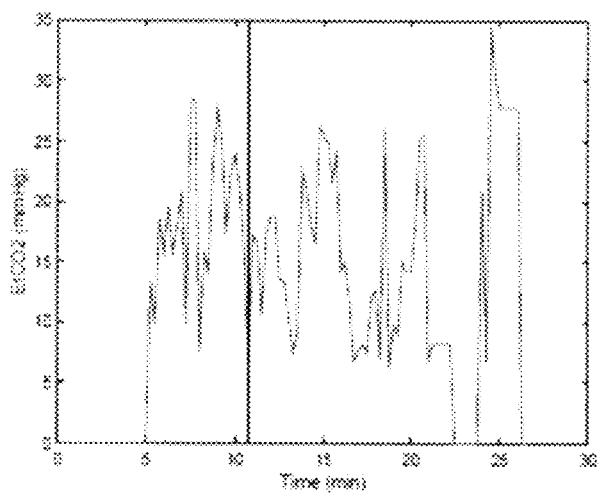
FIG. 11B is a graph depicting an instance in which the algorithm fails to detect the ET intubation time completely, in accordance with aspects of the invention.
Figure 12:
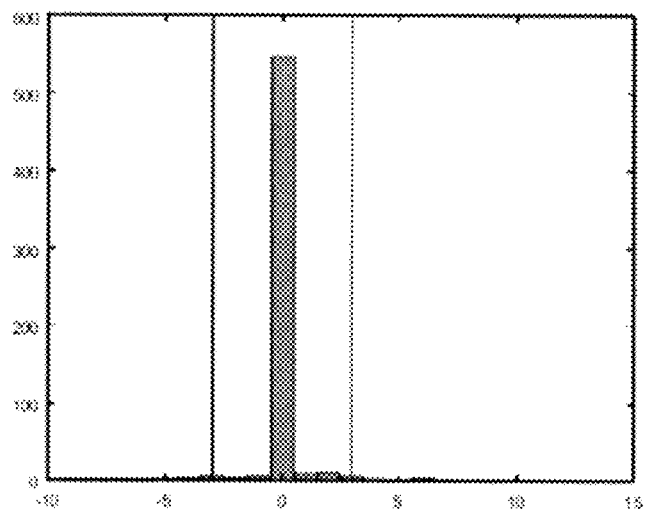
FIG. 12 is a histogram plot depicting the time difference between actual ET intubation time and the flagged ET intubation time determined by the algorithm, in accordance with aspects of the invention.

FIGS. 11A and 11B represent two samples of algorithm misdetection. In FIG. 11A, the algorithm detects the intubation five minutes earlier than its actual time, and in FIG. 11B the algorithm fails to detect the intubation time completely. These plots represent the patterns which lead to misdetection in the algorithm. By investigating the cases when the difference between actual and the detected intubation times is more than one minute, it was determined that the recordings are heavily affected by noise in all those cases. In four cases that the algorithm failed to converge, either the ET length was too short or the $EtCO_2$ was very low (less than 30 mmHg). The investigations showed that age or type of surgery has no effect on the algorithm's accuracy. FIG. 12 shows a histogram of the difference between actual intubation time and the detected intubation time. The vertical lines represent the range for a clinically valid detection. Table 5 (below) represents the number of times that each of the features exactly detected the intubation time. Table 5 shows that the variation index is the best feature in detecting intubation. Interestingly, the mean is the second best feature and variance is the third best feature. This table shows that the wavelet transform is efficient in analyzing the nonstationary nature of the $EtCO_2$ signal. Furthermore, the mean value has a high correlation with the intubation time.

TABLE 5

Breakdown of the detection accuracy of each of the three features

| Feature | Accuracy % |
|---|---|
| Mean | 79% |
| Variance | 72% |
| Variation Index | 85% |

Overview of Systems and Methods Using Algorithm for Detection of ET Intubation Time With reference to the exemplary system 100 embodied in FIG. 1, during anesthesia, the monitoring device 10 (for example, an anesthesia machine, mechanical ventilator, or respiratory function monitor) typically records the ventilation variables/respiratory parameters of the patient throughout the anesthesia procedure, including TV, $EtCO_2$, and PIP. A sensor module 60, which may be coupled to the is monitoring device 10, may have one or more sensors to capture respiratory rate, TV, PIP, or $EtCO_2$. A volume sensor 61 may be used to measure TV. A pressure sensor 62 may be used to measure PIP, and may also be useful for measuring TV. A $CO_2$ sensor 63 associated with the sensor module 60 may be used to measure $EtCO_2$. The $CO_2$ sensor may include a sampling line 63a attached to the airway device (e.g., ETT) 50 used to mechanically ventilate the pediatric patient. The sampling line 63a can be used to pull samples of $CO_2$ released by the respiratory system of the pediatric patient and to deliver the samples to the $CO_2$ sensor 63 for measurement.

The processor 20 can then use the recorded $EtCO_2$ respiratory parameter from the monitoring device 10 with the algorithm stored in the memory 30 to detect the time of ET intubation, and thereafter confirms the detection of ET intubation with the recorded TV or PIP, depending on the mode of ventilation used. When the processor 20 confirms the time of ET intubation using the algorithm, the processor 20 may transmit the confirmed detection to the monitoring device 10. The monitoring device 10 may then automatically record the processor's confirmed detection of ET intubation and chart the detected ET intubation time. This time-stamps the ET intubation time for further clinical decision making for the attending health care providers. The algorithm may therefore be used by a health care provider to prompt further treatment decisions in the event of a successfully confirmed and medically charted algorithmic detection of ET intubation time.

The processor 20 may also send a confirmation signal to an alert generator 40 if the ET intubation time detection is properly confirmed using the algorithm with TV or PIP. The alert generator 40 may then issue a confirmation message to the attending medical care providers about the confirmation, which may prompt them to carry out further medical decisions based on the confirmed ET intubation.

If the processor 20 fails to detect the intubation time using the recorded EtCO$_2$ and/or confirm the ET intubation detection time using either the TV or PIP with the algorithm (lack of convergence), the processor 20 will transmit a signal to the same or separate alert generator 40. The alert generator 40 will receive the signal and issue an alert to the attending medical care providers. Thus, the algorithm can also be used to indicate potential problems with the ET intubation procedure via an alert, which can prompt the attending medical care providers to make further clinical decisions to aid the anesthetized patient.

In the event of a failed detection and/or confirmation of ET intubation time, the processor 20 may also transmit this information to the monitoring device 10. The monitoring device 10 may also automatically record and medically chart this information to provide a record of a potential problem with ET intubation during the anesthesia (e.g., excessively "noisy" readings that prevent flagging or convergence of the algorithm, which may be indicative of improper ET intubation or leakage).

Figure 13:
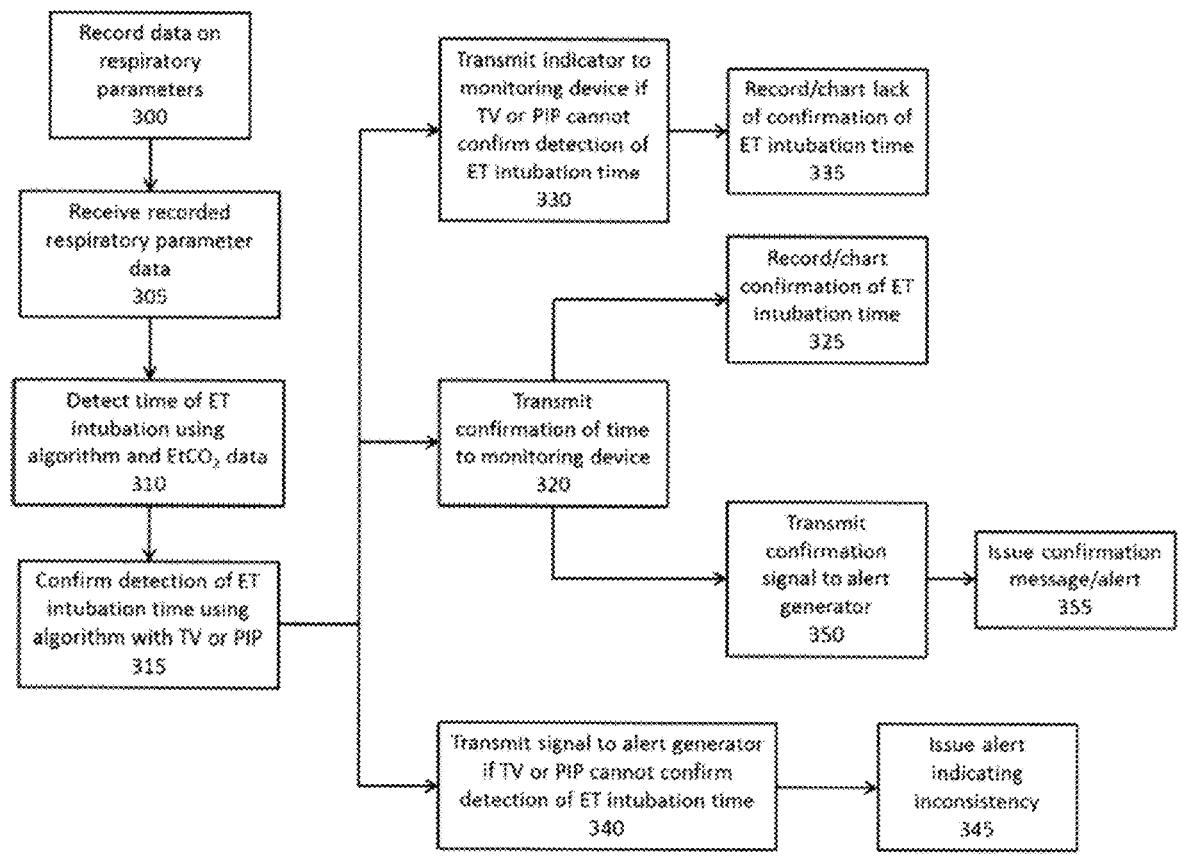
FIG. 13 is a flowchart depicting steps for detecting endotracheal intubation in accordance with aspects of the invention.

FIG. 13 depicts steps for detecting and confirming the time an ETT is placed during anesthesia of a pediatric patient. At step 300, the monitoring device 10 records data on respiratory parameters of the patient during the anesthesia procedure, including tidal volume (TV), end-tidal CO$_2$ (ETCO$_2$), and peak inspiratory pressure (PIP). At step 305, a processor 20 may receive the recorded respiratory parameter data, and may use an algorithm configured to detect the time of ET intubation with the EtCO$_2$ data at step 310 to determine the time of ET intubation of the patient. The algorithm may be stored in a memory 30. Then, the processor 20 confirms the detection of the ET intubation using the algorithm with the TV or PIP data (depending on the mode of mechanical ventilation) at step 315. The processor 20 may then transmit the confirmation of the detected time to the monitoring device 10 at step 320.

If the confirmation is transmitted to the monitoring device 10, then the confirmation may be automatically recorded and/or medically charted by the monitoring device 10 at step 325. If the processor 20 cannot confirm the time of ET intubation using the recorded TV or PIP data with the algorithm, then the processor 20 may transmit an indication to the monitoring device 10 at step 330. At step 335, the monitoring device 10 may then automatically chart and/or record the indication from the processor 20 that the processor 20 was unable to confirm the ET intubation time.

Additionally, if the processor 20 cannot confirm the ET intubation time with the algorithm and additional TV/PIP data, then the processor 20 may transmit a signal to an alert generator 40 at step 340. At step 345, the alert generator 40 receives the signal and may then issue an alert to the attending medical care providers that there was no confirmation. This provides the medical care providers with a prompt to investigate whether the ET intubation was successful.

The processor 20 may also transmit a confirmation signal to the alert generator at is step 350 if the recorded data of the TV and/or PIP confirms the ET intubation time with the algorithm. At step 355, the alert generator 40 may receive the confirmation signal and issue a confirmation message to the attending medical care providers, which alerts them to proceed with clinical decision-making upon confirming ET intubation time.

Summary Regarding Designed Algorithm for Detecting ET Intubation

An algorithm for the automatic detection of endotracheal intubation was developed based on the variables recorded by an anesthesia machine, mechanical ventilator, or a respiratory function monitor, principally, end-tidal carbon dioxide (EtCO$_2$), tidal volume (TV) and peak inspiratory pressure (PIP). The algorithm uses EtCO$_2$ to flag candidate intubation times, following which TV or PIP was used to detect exact intubation time. It was found that EtCO$_2$ is the most reliable variable for detecting intubation in mechanical ventilation since its morphology is not affected by the mode of ventilation. Three features were extracted from the data in order to capture the trend of EtCO$_2$ during intubation. Based on each of these features, an intubation time was flagged. To detect the exact intubation time we use TV or PIP based on the mode of mechanical ventilation. The results of testing the algorithm on real data collected from inpatient operating rooms demonstrate the excellent performance of the algorithm. Application of the wavelet transforms makes the algorithm robust to noise inherent in the data collection. Additionally, validation of the results of EtCO$_2$ data with TV and PIP ensures the consistency of the algorithm and makes it independent of the mechanical ventilation mode. The results of the algorithm are naturally limited by the sampling rate of the data collection. Better sampling rate can be expected to improve the performance of the algorithm.

Although the inventions are illustrated and described herein with reference to specific embodiments, the inventions are not intended to be limited to the details shown. Rather, various modifications may be made in the details within the scope and range of equivalents of the claims and without departing from the inventions. While preferred embodiments of the inventions have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the inventions.

What is claimed:

1. A system for confirming a type of a mechanical ventilation airway device used during an anesthesia procedure on a pediatric patient, the mechanical ventilation airway device configured to generate and regulate a flow of air to a respiratory system of the pediatric patient during the anesthesia procedure, the system comprising:
   a monitoring device configured to:
      monitor respiratory parameters of the pediatric patient during the anesthesia procedure, the respiratory parameters including respiratory rate (RR), tidal volume (TV), end-tidal carbon dioxide (EtCO$_2$), and peak inspiratory pressure (PIP), and
      receive a mechanical ventilation airway device selection for the anesthesia procedure;

a memory including a machine-learning data mining algorithm configured to identify the type of the mechanical ventilation airway device used for the anesthesia procedure;
an alert generator configured to:
  receive an alert signal, and
  issue an alert in response to the alert signal; and
a processor coupled to the monitoring device, the memory, and the alert generator, the processor configured to:
  receive the monitored respiratory parameters,
  identify the type of the mechanical ventilation airway device by applying the machine-learning data mining algorithm to the monitored respiratory parameters,
  determine consistency of the identified type of the mechanical ventilation airway device and the mechanical ventilation airway device selection, and
  transmit, to the alert generator, the alert signal if the identified type of the mechanical ventilation airway device and the mechanical ventilation airway device selection are determined to be inconsistent.

2. The system of claim 1, wherein the processor is further configured to transmit a confirmation signal to the alert generator if the identified type of the mechanical ventilation airway device and the mechanical ventilation airway device selection are consistent, and wherein the alert generator is further configured to issue a confirmation message in response to the confirmation signal.

3. The system of claim 1, wherein the machine-learning data mining algorithm is at least one of a boosted trees (BT) classifier, a support vector machine (SVM) classifier, or a neural network (NN) classifier.

4. The system of claim 1, wherein the monitoring device is one of an anesthesia machine, a respiratory function monitor, or a mechanical ventilator.

5. The system of claim 1, wherein the monitoring device comprises a sensor module for detecting at least one of RR, TV, PIP, or $EtCO_2$.

6. The system of claim 5, wherein the sensor module comprises at least one of a volume sensor, a pressure sensor, or a $CO_2$ sensor.

7. The system of claim 1, wherein the system further comprises:
  a $CO_2$ sensor; and
  a sampling line, coupled to the mechanical ventilation airway device and coupled to the $CO_2$ sensor, configured to deliver samples of $CO_2$ released by the respiratory system of the pediatric patient to the $CO_2$ sensor.

8. A method for confirming a type of a mechanical ventilation airway device used during an anesthesia procedure on a pediatric patient, the mechanical ventilation airway device configured to generate and regulate a flow of air to a respiratory system of the pediatric patient during the anesthesia procedure, the method comprising:
  monitoring, with a monitoring device, respiratory parameters of the pediatric patient during the anesthesia procedure, the respiratory parameters including respiratory rate (RR), tidal volume (TV), end-tidal carbon dioxide ($EtCO_2$), and peak inspiratory pressure (PIP);
  recording, with the monitoring device, a mechanical ventilation airway device selection for the pediatric patient;
  identifying, with a processor, the type of the mechanical ventilation airway device by applying a machine-learning data mining algorithm stored in a memory to the monitored respiratory parameters, the machine-learning data mining algorithm configured to determine the type of mechanical ventilation airway device used for the anesthesia;
  determining, with the processor, consistency of the identified type of mechanical ventilation airway device and the mechanical ventilation airway device selection;
  transmitting, with the processor to an alert generator, an alert signal if the identified type of mechanical ventilation airway device and the mechanical ventilation airway device selection are inconsistent; and
  issuing, with the alert generator, an alert in response to the alert signal.

9. The method of claim 8, further comprising the steps of:
  transmitting, with the processor, a confirmation signal to the alert generator if the identified type of mechanical ventilation airway device and the mechanical ventilation airway device selection are consistent; and
  issuing, with the alert generator, a confirmation message in response to the confirmation signal.

10. The method of claim 8, wherein the machine-learning data mining algorithm is at least one of a boosted trees (BT) classifier, a support vector machine (SVM) classifier, or a neural network (NN) classifier.

11. The method of claim 8, wherein the monitoring device is one of an anesthesia machine, a respiratory function monitor, or a mechanical ventilator.

12. The method of claim 8, further comprising sensing, with a sensor module of the monitoring device, at least one of the respiratory parameters RR, TV, PIP, or $EtCO_2$.

13. The method of claim 12, further comprising:
  sampling, with a sampling line coupled to the selected mechanical ventilation airway device and coupled to a $CO_2$ sensor of the sensor module, CO2 released by the respiratory system of the pediatric patient;
  delivering, with the sampling line, the sampled $CO_2$ to the $CO_2$ sensor; and
  sensing, with the $CO_2$ sensor, the delivered $CO_2$.

14. A system for detecting a time of intubation with an endotracheal tube during an anesthesia procedure on a pediatric patient, the system comprising:
  a monitoring device configured to:
    monitor respiratory parameters of the pediatric patient during the anesthesia procedure, the respiratory parameters of the anesthesia procedure including tidal volume (TV), and end-tidal carbon dioxide ($ETCO_2$), and
    record a confirmed endotracheal intubation time; and
  a processor coupled to the monitoring device, the processor configured to:
    receive the monitored respiratory parameters of the pediatric patient from the monitoring device,
    identify at least one candidate time during the anesthesia procedure by periodically calculating a plurality of statistical features for the monitored $EtCO_2$ respiratory parameter,
    confirm one of the at least one candidate time as the confirmed endotracheal intubation time by determining a mean increase in the TV respiratory parameter at each of the at least one candidate time and selecting the candidate time corresponding to the largest mean increase in the TV respiratory parameter, and
    transmit, to the monitoring device, the confirmed endotracheal intubation time.

15. The system of claim 14, further comprising:
an alert generator configured to:
  receive an alert signal; and issue an alert in response to the alert signal wherein the processor is further coupled to the alert generator and is configured to transmit, to the alert generator, the alert signal if the processor cannot detect the time of endotracheal intubation or if the processor cannot confirm the detection of the time of endotracheal intubation.

16. The system of claim 15, wherein:
the processor is further coupled to the alert generator and is configured to transmit a confirmation signal to the alert generator if the detection of the time of endotracheal intubation is confirmed; and
the alert generator is further configured to issue a confirmation message in response to the confirmation signal.

17. The system of claim 14, wherein the monitoring device is one of an anesthesia machine, a respiratory function monitor, or a mechanical ventilator.

18. The system of claim 14, wherein the monitoring device comprises a sensor module configured to detect at least one of TV, PIP, or $EtCO_2$.

19. The system of claim 18, wherein the sensor module comprises at least one of a volume sensor, a pressure sensor, or a $CO_2$ sensor.

20. The system of claim 14, wherein the system comprises:
a $CO_2$ sensor; and
a sampling line coupled to the $CO_2$ sensor and coupled to the endotracheal tube, configured to deliver samples of $CO_2$ released by the respiratory system of the pediatric patient to the $CO_2$ sensor.

21. A system for detecting a time of intubation with an endotracheal tube during an anesthesia procedure on a pediatric patient, the system comprising:
a monitoring device configured to:
monitor respiratory parameters of the pediatric patient during the anesthesia procedure, the respiratory parameters of the anesthesia procedure including end-tidal carbon dioxide ($ETCO_2$) and peak inspiratory pressure (PIP), and
record a confirmed endotracheal intubation time; and
a processor coupled to the monitoring device, the processor configured to:
receive the monitored respiratory parameters of the pediatric patient from the monitoring device,
identify at least one candidate time during the anesthesia procedure by periodically calculating a plurality of statistical features for the monitored $EtCO_2$ respiratory parameter,
confirm one of the at least one candidate time as the confirmed endotracheal intubation time by determining a mean increase in the PIP respiratory parameter at each of the at least one candidate time and selecting the candidate time corresponding to the largest mean increase in the PIP respiratory parameter, and
transmit, to the monitoring device, the confirmed endotracheal intubation time.

22. The system of claim 21, further comprising:
an alert generator configured to:
receive an alert signal; and
issue an alert in response to the alert signal
wherein the processor is further coupled to the alert generator and is configured to transmit, to the alert generator, the alert signal if the processor cannot detect the time of endotracheal intubation or if the processor cannot confirm the detection of the time of endotracheal intubation.

23. The system of claim 22, wherein:
the processor is further coupled to the alert generator and is configured to transmit a confirmation signal to the alert generator if the detection of the time of endotracheal intubation is confirmed; and
the alert generator is further configured to issue a confirmation message in response to the confirmation signal.

24. The system of claim 21, wherein the monitoring device is one of an anesthesia machine, a respiratory function monitor, or a mechanical ventilator.

25. The system of claim 21, wherein the monitoring device comprises a sensor module configured to detect at least one of PIP or $EtCO_2$.

26. The system of claim 25, wherein the sensor module comprises at least one of a volume sensor, a pressure sensor, or a $CO_2$ sensor.

27. The system of claim 21, wherein the system comprises:
a $CO_2$ sensor; and
a sampling line coupled to the $CO_2$ sensor and coupled to the endotracheal tube, configured to deliver samples of $CO_2$ released by the respiratory system of the pediatric patient to the $CO_2$ sensor.

* * * * *